(12) United States Patent
Jungnickel et al.

(10) Patent No.: US 8,763,189 B2
(45) Date of Patent: Jul. 1, 2014

(54) ORAL HYGIENE IMPLEMENT

(75) Inventors: Uwe Jungnickel, Koenigstein/Taunus (DE); Niclas Altmann, Schoeneck (DE); René Guebler, Friedberg (DE)

(73) Assignee: Braun GmbH, Kronberg (DE)

( * ) Notice: Subject to any disclaimer, the term of this patent is extended or adjusted under 35 U.S.C. 154(b) by 91 days.

(21) Appl. No.: 13/464,210

(22) Filed: May 4, 2012

(65) Prior Publication Data

US 2013/0000059 A1   Jan. 3, 2013

Related U.S. Application Data

(60) Provisional application No. 61/482,888, filed on May 5, 2011.

(51) Int. Cl.
| | |
|---|---|
| *A46B 9/04* | (2006.01) |
| *A46B 13/02* | (2006.01) |
| *A46B 15/00* | (2006.01) |

(52) U.S. Cl.
USPC .......................................... 15/22.1; 15/167.1

(58) Field of Classification Search
USPC ....................................... 15/22.1, 105, 167.1
See application file for complete search history.

(56) References Cited

U.S. PATENT DOCUMENTS

| | | | |
|---|---|---|---|
| 4,802,255 A | 2/1989 | Breuer | |
| 5,268,005 A | 12/1993 | Suhonen | |
| 5,313,909 A | 5/1994 | Tseng | |
| 5,722,106 A | 3/1998 | Masterman | |
| 5,815,872 A | 10/1998 | Meginnis et al. | |
| 5,836,769 A | 11/1998 | Spencer | |
| 5,980,542 A | 11/1999 | Saldivar | |
| 6,018,840 A | 2/2000 | Guay | |
| 6,058,541 A | 5/2000 | Masterman | |
| 6,102,923 A | 8/2000 | Murayama | |
| 6,151,745 A | 11/2000 | Roberts | |
| 6,389,636 B1 | 5/2002 | Savill | |
| 6,402,768 B1 | 6/2002 | Liebel | |
| 6,475,553 B2 | 11/2002 | Guay | |
| 6,553,604 B1 | 4/2003 | Braun | |
| 6,954,961 B2 | 10/2005 | Ferber et al. | |
| 7,024,717 B2 | 4/2006 | Hilscher | |
| 7,086,111 B2 | 8/2006 | Hilscher | |
| 7,207,080 B2 | 4/2007 | Hilscher | |
| 7,942,667 B2 * | 5/2011 | Rizoiu et al. ................ 433/29 |
| 2002/0129454 A1 | 9/2002 | Hilscher et al. | |
| 2004/0134007 A1 | 7/2004 | Davies | |
| 2004/0154112 A1 | 8/2004 | Braun | |

(Continued)

FOREIGN PATENT DOCUMENTS

| | | |
|---|---|---|
| EP | 2229917 | 9/2010 |
| WO | WO 2010/106524 | * 9/2010 |

OTHER PUBLICATIONS

International Search Report, date mailed Apr. 12, 2012, 4 pages.

*Primary Examiner* — Randall Chin
(74) *Attorney, Agent, or Firm* — John P. Colbert

(57) ABSTRACT

An oral hygiene implement is provided. The oral hygiene implement includes a handle; a head including a plurality of contact elements; a neck disposed between the handle and the head; an indication element; and an electromagnetic energy output source. The electromagnetic energy is directed from the output source to the indication element such that a Total Visible Projected Angle ($\phi_T$) of the oral hygiene implement is greater than about 300 degrees.

16 Claims, 27 Drawing Sheets

(56) References Cited

U.S. PATENT DOCUMENTS

| | | |
|---|---|---|
| 2004/0255416 A1 | 12/2004 | Hohlbein |
| 2005/0000043 A1 | 1/2005 | Chan |
| 2005/0000049 A1 | 1/2005 | Hohlbein |
| 2005/0038461 A1 | 2/2005 | Phillips |
| 2005/0053895 A1 | 3/2005 | Pinyayev et al. |
| 2005/0053896 A1 | 3/2005 | Pinyayev et al. |
| 2005/0166344 A1 | 8/2005 | Hohlbein |
| 2005/0210612 A1 | 9/2005 | Hohlbein |
| 2006/0010628 A1 | 1/2006 | Moskovich |
| 2006/0026784 A1 | 2/2006 | Moskovich |
| 2006/0052806 A1 | 3/2006 | Xi |
| 2006/0080794 A1 | 4/2006 | Punshon |
| 2006/0195995 A1 | 9/2006 | Moskovich |
| 2006/0272112 A9 | 12/2006 | Braun |
| 2007/0049956 A1 | 3/2007 | Mythen |
| 2007/0251040 A1 | 11/2007 | Braun |
| 2008/0060148 A1* | 3/2008 | Pinyayev et al. ............ 15/22.1 |
| 2008/0189888 A1 | 8/2008 | Hohlbein |
| 2008/0244849 A1 | 10/2008 | Moskovich |
| 2009/0246430 A1 | 10/2009 | Kriegel |
| 2010/0028512 A1 | 2/2010 | Kriegel |

* cited by examiner

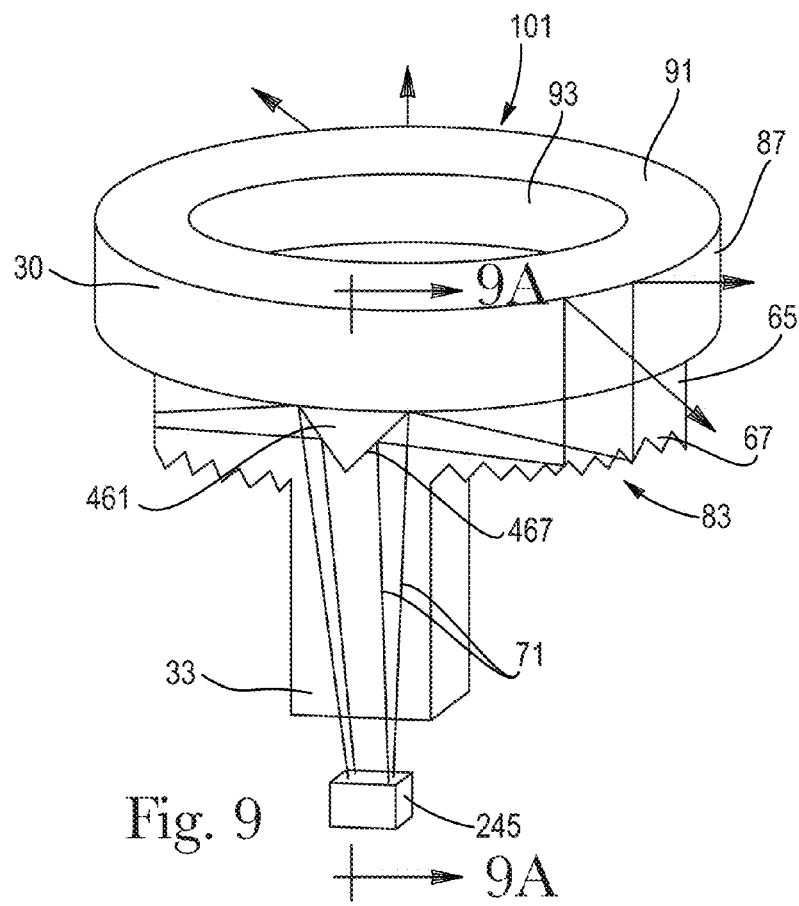
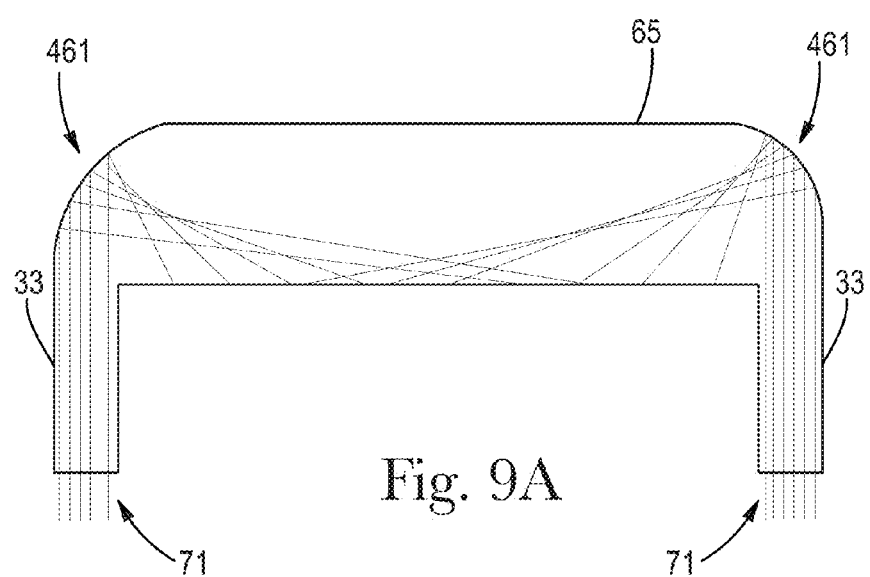

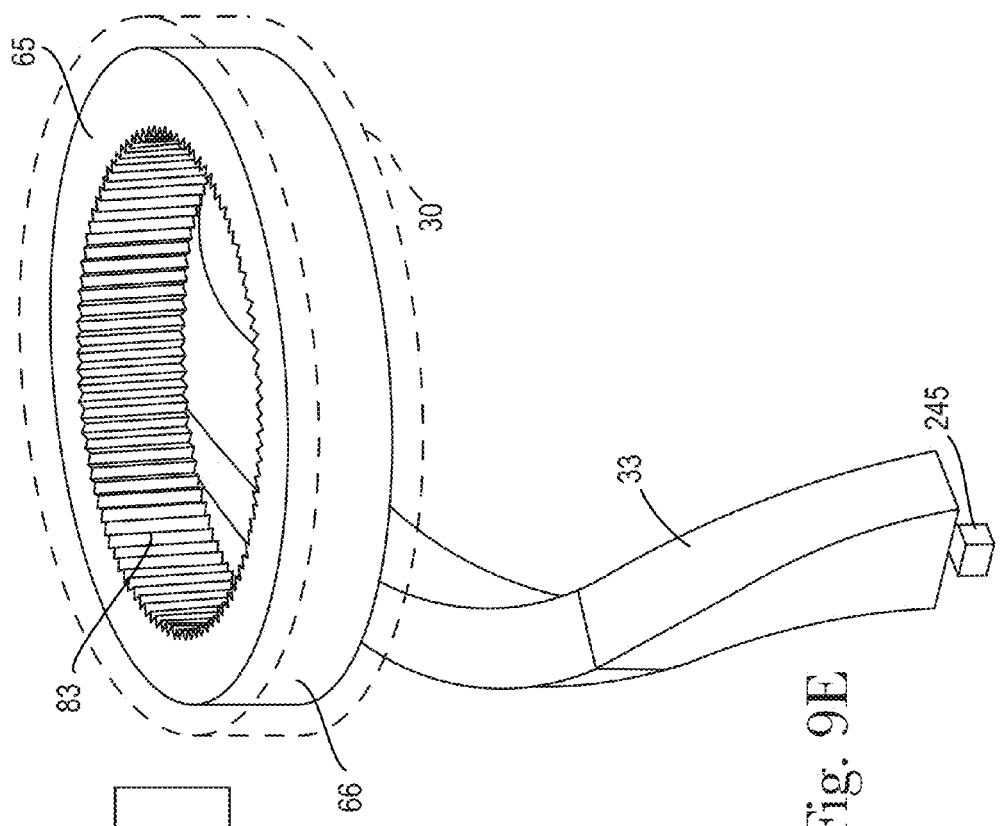
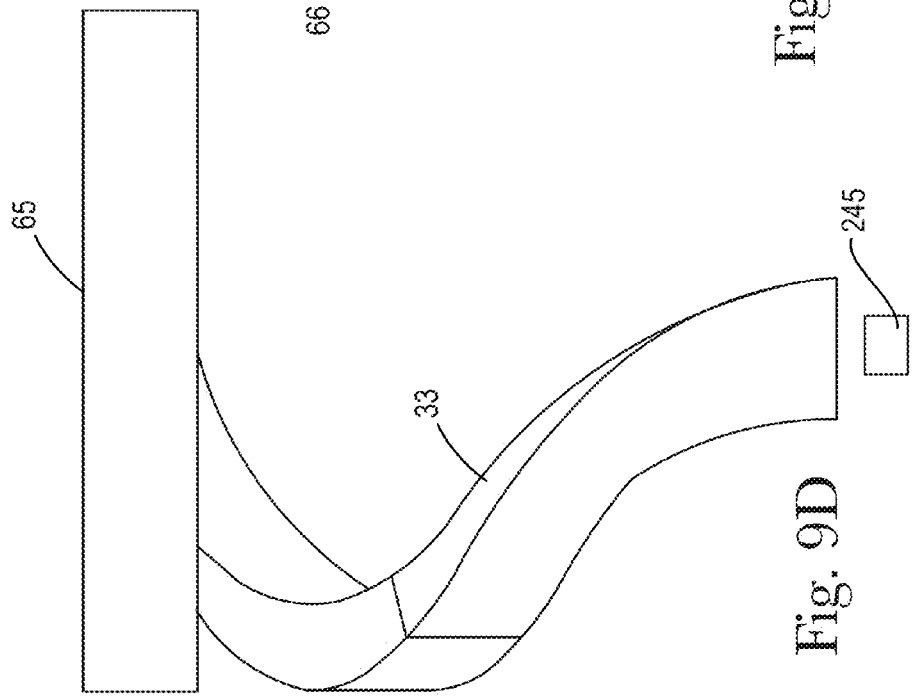
Fig. 9E
Fig. 9D

US 8,763,189 B2

ORAL HYGIENE IMPLEMENT

CROSS REFERENCE OF RELATED APPLICATION

This application claims the benefit of provisional application Ser. No. 61/482,888, filed on 5 May 2011, which is incorporated by reference herein in its entirety.

FIELD OF THE INVENTION

The present disclosure relates generally to an oral hygiene implement, and more particularly to an oral hygiene implement including an indication element that exhibits an enhanced light distribution, resulting in facilitating consumers' identification and understanding of various brushing conditions, for example, optimal applied brushing force, via visible signals.

BACKGROUND OF THE INVENTION

The utilization of toothbrushes to clean teeth has long been known. There are two main classes of toothbrushes available for a user, manual toothbrushes and power toothbrushes. For manual toothbrushes the user generally provides the majority of the cleaning motion. In contrast, for power toothbrushes the majority of the cleaning motion is provided by the toothbrush. The power toothbrush generally includes a drive mechanism for driving a brush head. Because the toothbrush includes a drive mechanism, power toothbrushes are generally more costly to produce than manual toothbrushes. Power toothbrushes may provide a user with additional features as well. For example, some power toothbrushes can track the time that a brush head is used and indicate to the user the time for replacement of the brush head. As another example, some power toothbrushes can provide an indication to the user as to when the user brushes a predetermined amount of time.

These indication means have traditionally been positioned in the front of the toothbrush, the area or side having the bristles. However during use a toothbrush is moved in many directions, such that an indication means positioned in only one side or area of a toothbrush may not always be visible to a user. Accordingly, a need exists for a personal hygiene implement which can provide the user with an indication means that is visible during use.

SUMMARY OF THE INVENTION

In one embodiment, an oral hygiene implement includes a handle; a head including a plurality of contact elements; a neck disposed between the handle and the head; an indication element; and an electromagnetic energy output source. The electromagnetic energy is directed from the output source to the indication element such that a Total Visible Projected Angle ($\phi_T$) of the oral hygiene implement is greater than about 300 degrees.

In another embodiment, an oral hygiene implement includes a handle; a head including a plurality of contact elements; a neck disposed between the handle and the head; an indication element; and an electromagnetic energy output source. The electromagnetic energy is directed from the output source to the indication element such that a Visible Projected Angle ($\phi_1$) of the oral hygiene implement is greater than about 130 degrees.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIG. 9 is a perspective view of an indicator mechanism according to one embodiment illustrated and described herein;

FIG. 9A is a flattened illustrative view of FIG. 9 sectioned through section line 9A-9A;

FIG. 9D is a side view of a transmission element and transmission element ring according to one embodiment illustrated and described herein;

FIG. 9E is a perspective view of a transmission element and transmission element ring according to one embodiment illustrated and described herein;

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

As used herein "personal hygiene implement" refers to any implement which can be utilized for the purposes of personal hygiene. Some suitable examples include oral hygiene implements, such as toothbrushes, either manual or powered; razors, either manual or powered; shavers, either manual or powered; trimmers, etc.

As used herein, "oral hygiene implement" refers to any device which can be utilized for the purposes of oral hygiene. Some suitable examples of such devices include toothbrushes (both manual and power), flossers (both manual and power), water picks, irrigators and the like.

For ease of explanation, the oral hygiene implement described hereafter shall be a powered toothbrush; however, as stated above, an oral hygiene implement constructed in accordance with the present disclosure is not limited to a powered toothbrush construction. Additionally, the embodiments described hereafter are equally applicable to blades, razors, other personal hygiene implements, or the like.

Figure 1:
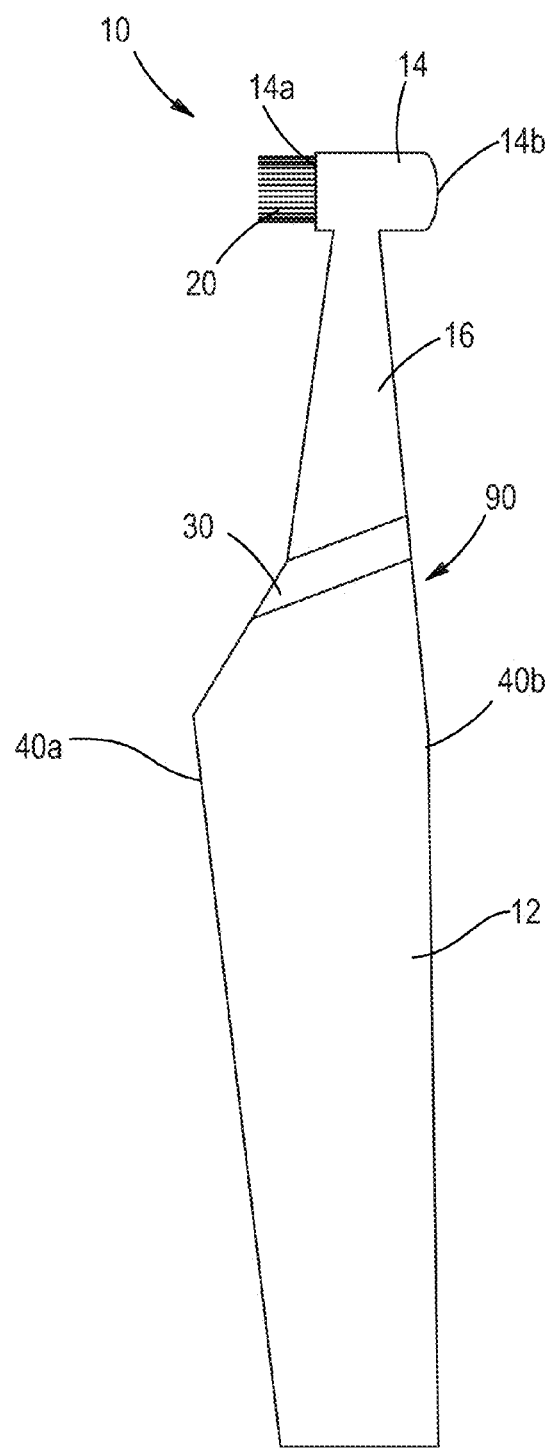
FIG. 1 is a side view showing an oral hygiene implement, for example a toothbrush, according to one embodiment illustrated and described herein.

As shown in FIG. 1, a toothbrush 10 comprises a handle 12, a head 14, and a neck 16 extending between the handle 12 and the head 14. A contact element field 20 comprising one or more contact elements extends from a first surface 14A of the head 14. A tongue cleaner, soft tissue cleanser, massaging element, or the like, may be disposed on a second surface 14B of the head 14. The tongue cleaners, soft tissue cleansers, massaging elements, or the like, are discussed hereafter.

An indication element 30 may be disposed between the handle 12 and the neck 16 adjacent the proximal end 90. The indication element 30 may provide a visible signal to a user for a plurality of conditions. For example, the visible signal may be provided when a user has brushed for an adequate amount of time, for example two minutes, when the toothbrush needs to be replaced, or when the user is brushing too hard as excess pressure can damage gums.

The indication element 30 may be positioned in any suitable location on the toothbrush 10. For example, in some embodiments, the indication element 30 may surround the neck 16 or may surround the handle 12. In one embodiment, the indication element 30 is in the form of a ring, circle, loop, hoop, disc, band, halo, sphere or any other suitable shape that provides a user good visibility from all sides. As another example, the indication element 30 may surround a portion of the handle 12, a portion of the neck 16, or both. As yet another example, the indication element 30 may be disposed on a back-facing surface 40B of the handle 12, neck 16, or both. As yet another example, the indication element 30 may be disposed on a front-facing surface 40A of the handle 12, neck 16, or both.

Figure 2:
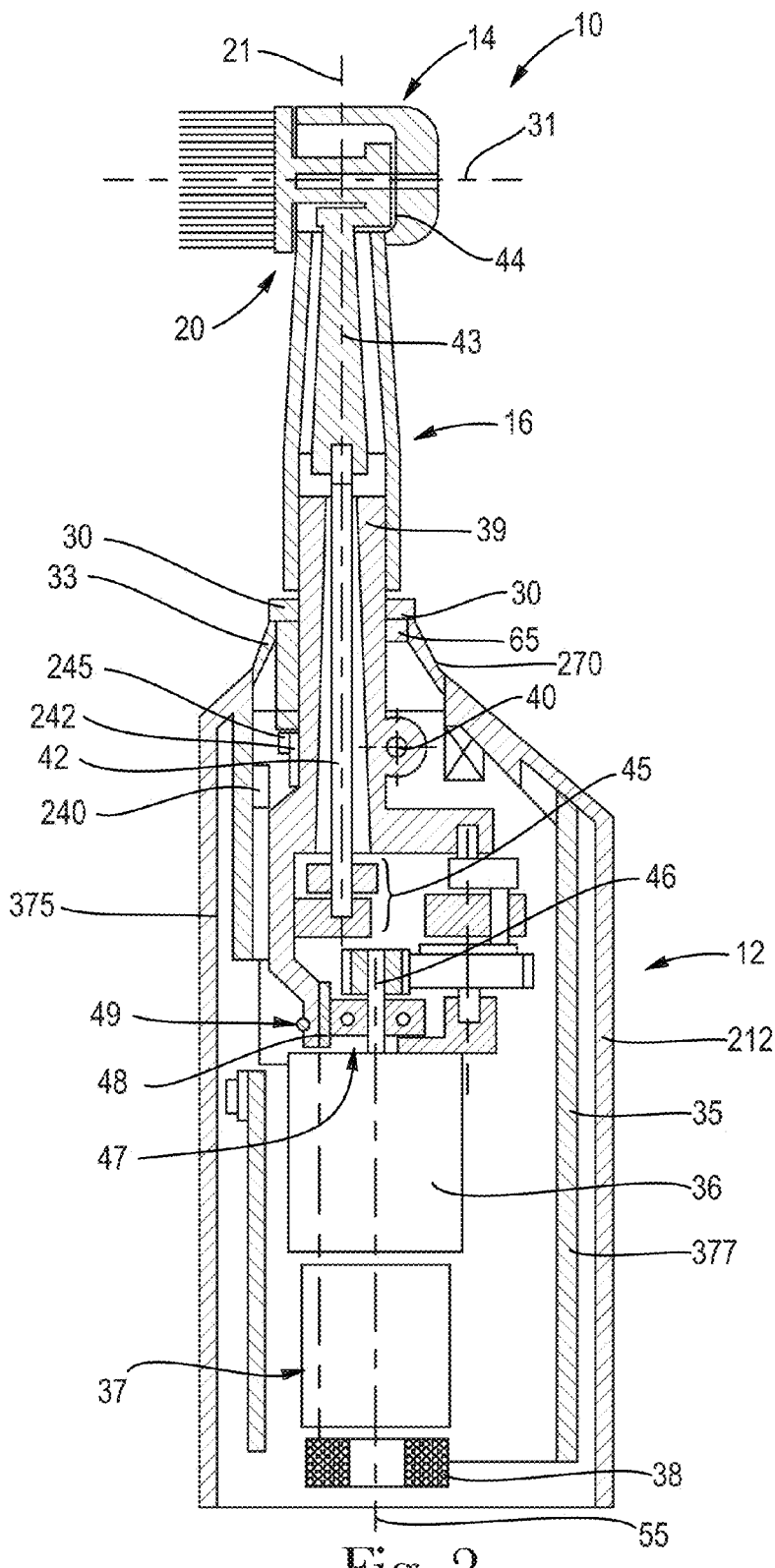
FIG. 2 is a plan view showing an oral hygiene implement, for example a toothbrush, according to one embodiment illustrated and described herein.

Referring to FIGS. 1 and 2, the contact field element 20 may be mounted on the head 14 such that it can be rotated about an axis 31. The axis 31 can be perpendicular to the longitudinal axis 21 of the neck 16. The axis 31 may also be angled relative to the longitudinal axis 21 of the neck 16. The handle 12 comprises an outer shell 212, forming an interior section of the handle 12, with a chassis 35 disposed therein. Fastened onto the chassis 35 are a drive motor 36, a power source, such as a battery 37, and other electronic components, for example, a charging coil 38. Further, a rocker 39 may be mounted on the chassis 35 such that it can be pivoted about a rocker axis 40. The rocker axis 40 extends transversely to the longitudinal axis 55 of handle 12. The rocker 39 projects out of handle 12. The neck 16 may be releasably attached to the projecting end of rocker 39. As a result, the neck 16 can be rocked, along with rocker 39, about rocker axis 40.

The annular space between the rocker 39 and the outer shell 212 of the handle be sealed by a sealing element 270; thereby reducing the likelihood of leakage into the cavity of the outer shell 212. The sealing element 270 may comprise any suitable sealing feature. Some examples of sealing features include deformable materials which can be compressed and then recover within the cavity of the outer shell 212, o-rings, etc. In some embodiments, a soft material may be overmolded onto the chassis 35, and during assembly of the chassis 35 and outer shell 212 the soft material may engage the outer shell 212 to form a seal. In other embodiments, a soft material may be overmolded to the outer shell 212, and subsequently the chassis 35 may be inserted into the outer shell 212 and engage the soft material. Still in other embodiments, a soft material may be a discrete element which is either placed on the chassis 35 before attachment of the chassis 35 to the outer shell 212 or is placed on the outer shell 212 prior to the attachment of the chassis 35 to the outer shell 212. In certain embodiments the indication element 30 can seal the annular space between the rocker 39 and the outer shell 212.

Additionally, in certain embodiments, electromagnetic energy, such as light provided to the indication element 30 may also be provided to the sealing element 270. In the case where the sealing element 270 is transparent, light may be provided to the user via the indication element 30 and the sealing element 270. In the case where the sealing element 270 is translucent, the light may have an intensity or color contrast between the light of the sealing element 270 and the indication element 30. In the case where the sealing element 270 is pigmented and translucent or transparent, the light provided to the indication element 30 may blend with the pigment color of the sealing element 270 to produce a unique visual effect. Accordingly, the light provided may comprise a first color while the pigmented sealing element 270 may comprise a second color.

A first drive shaft 42 is disposed within the interior of the rocker 39. In embodiments having a detachable head 14 and neck 16, when the neck 16 is attached to the handle 12, the first drive shaft 42 engages in a rotationally fixed manner with a second drive shaft 43. The second drive shaft 43 then drives the contact field element 20 in rotation about the axis of rotation 31 via a bevel-gear stage 44. The motor end of first drive shaft 42 is connected to drive motor 36 via a gear mechanism 45. The powered toothbrush 10 further includes, within the handle 12, a motor shaft 46 that projects out from drive motor 36. The continuous rotary movement of motor shaft 46 is converted into a rotary, oscillating movement of first drive shaft 42 by means of gear mechanism 45. The result is that contact field element 20 is driven in rotation in a reciprocating manner.

In certain embodiments, a translatory stroke or picking movement of contact field element 20 along axis 31 may be produced by the pivotable arrangement of rocker 39. The rocker 39 is seated on a cyclically movable drive part 47 (here, a cam), which is designed as an eccentric and is itself seated on the motor shaft 46. The end of the rocker 39 that is directed away from contact field element 20 forms a follower part 48. The follower part 48 follows the curved surface or cyclic movement of the cam 47, so that rocker 39 executes a reciprocating rocking movement. For this purpose, a prestressing device 49, for example a spring, biases the follower part 48 of the rocker 39 against cam 47. The biasing, via rocker 39, forces the contact field element 20 in the direction of its operating side, while the cam 47, by way of its corresponding curved surface, forces the contact field element 20 in the opposite direction.

A variety of electronic elements may be disposed within the outer shell 212. For example, within the outer shell 212 there may be housed, a timing circuit, a processor 240, a printed circuit board (PCB) 242, or electromagnetic output sources (output sources) 245, for example, audible sources, light sources, LED's, or combinations thereof. The outer shell 212 may accommodate a plurality of power sources where additional voltage is required, for example to provide threshold voltage for an LED.

Figure 3A:
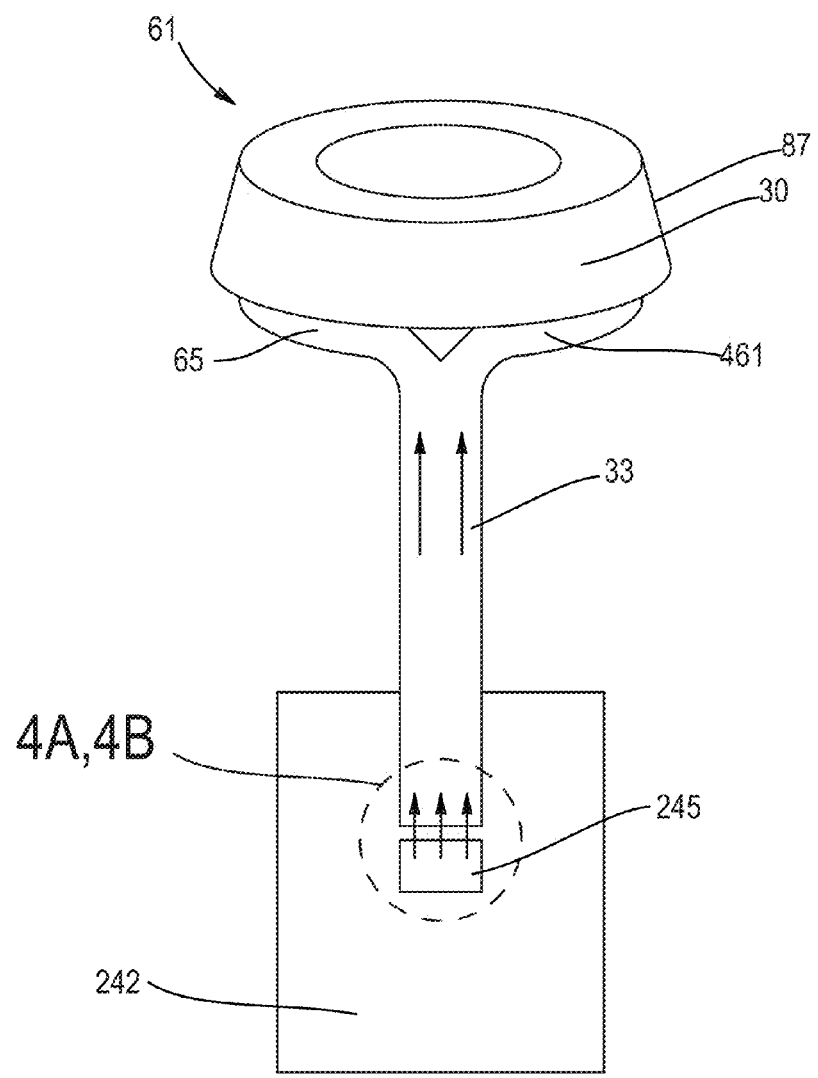
FIG. 3A is a frontal view showing an indicator mechanism according to one embodiment illustrated and described herein.

The chassis 35 can provide support for the processor 240, or the output source 245. The power source 37 can be electrically connected with the processor 240, PCB 242, or both, and the processor 240 or PCB 242 can be electrically connected with the output source 245. As shown in FIG. 2 and FIG. 3A the output source 245, for example an LED, may be in electromagnetic communication with a transmission element 33. The transmission element 33 can transmit electromagnetic energy, such as light from the output source 245 to a transmission element ring 65 and the indication element 30.

Figure 3B:
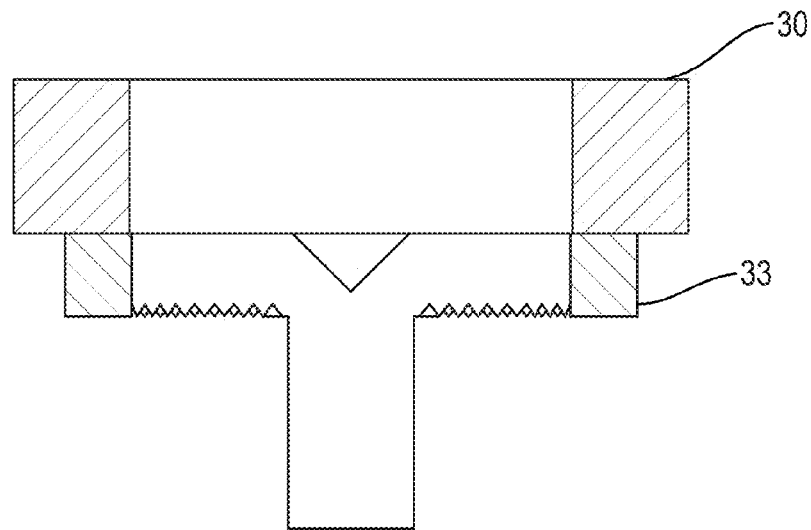
FIG. 3B is a cross-sectional view of an indicator mechanism according to one embodiment illustrated and described herein.
Figure 3C:
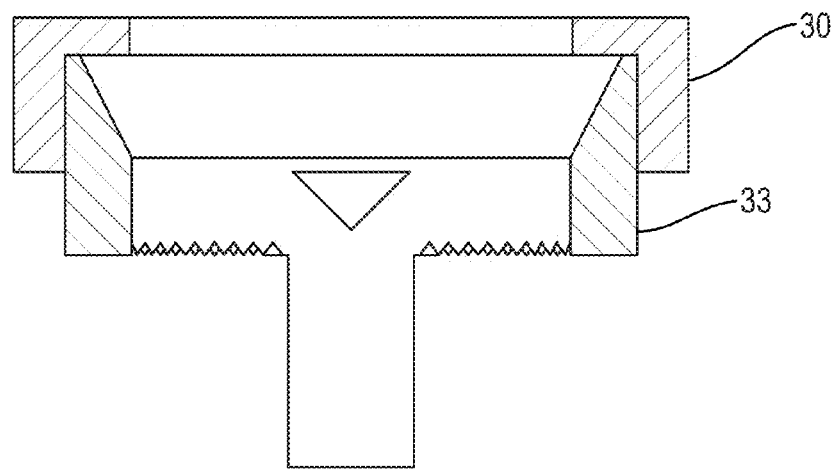
FIG. 3C is a cross-sectional view of an indicator mechanism according to one embodiment illustrated and described herein.

Referring to FIG. 3A, an indicator mechanism 61 is shown, which in this embodiment comprises a transmission element 33, transmission element ring 65, and an indication element 30. The transmission element 33 is configured to transmit electromagnetic energy, such as light from an output source 245 to the indication element 30. For example, where the output source 245 is an LED, the transmission element 33 may be a light pipe, light guide, fiber optic, or the like. A transmission element 33 may also comprise a transmission element ring 65. The transmission element ring 65 laterally extends from the transmission element 33 such that it partially or completely traverses the circumference of the toothbrush handle, so as to spread the distribution of light throughout the indication element 30. The material selected for the transmission element 33 can be a clear material, transparent material, translucent material, or combinations thereof, which transmit light from the LED through the transmission element 33 to the indication element 30. Some examples of suitable materials for the transmission element 33 include glass, polymethylmethacrylate, polycarbonate, copolyester, polypropylene, polyethyleneteraphthalate, silicone, combinations thereof, for example polyester and polycarbonate, or the like, In some embodiments, the indication element 30 and the transmission element 33 may be unitary. For example, the transmission element 33 and the indication element 30 may be integrally constructed out of a first material during an injection molding process. In some embodiments, transmission element 33 may be a discrete part from the indication element 30. In those embodiments where the transmission element 33 and indication element 30 are discrete parts, the elements 30, 33 may be positioned relative to each other in any manner that allows the transmission of electromagnetic energy from the output source 245, through the transmission element 33 to the indication element 30. For example, as shown in FIG. 3B the indication element 30 may be positioned above the transmission element 33 or as shown in FIG. 3C the transmission element 33 may be partially nested within the indication element 30. With reference back to FIG. 2, in some embodiments, the indication element 30, the transmission element 33, and chassis 35 may be integrally formed. In some embodiments, the indication element 30 and transmission element 33 may be integrally formed and subsequently attached to the chassis 35. In some embodiments, the indication element 30, the transmission element 33, and outer shell 212 may be integrally formed. In some embodiments, the indication element 30 and the outer shell 212 may be integrally formed and the transmission element 33 will be subsequently attached to the outer shell 212. The benefit of such embodiments is that a reduced number of components are required for the brush which can reduce the cost and/or time of assembly.

The transmission element 33 may transmit electromagnetic energy, such as light, to the indication element 30 by internal reflection or external reflection. External reflections are reflections where the light originates in a material of low refractive index (such as air) and reflects off of a material with a higher refractive index (such as aluminum or silver). A common household mirror operates on external reflection.

Internal reflections are reflections where the light originates in a material of higher refractive index (such as polycarbonate) and reflects off of a material with lower refractive index (such as air or vacuum or water). Fiber optic technology operates on the principle of internal reflections. Refractive index is an optic attribute of any material which measures the tendency of light to refract, or bend, when passing through the material. Even materials that do not conduct light (such as aluminum) have indices of refraction.

Typically, external reflections are most efficient when the angle of incidence of the light is near-normal (i.e., light approaches perpendicular to the surface) and degrade as the angle of incidence increases (approaches the surface at a steep angle). Conversely, internal reflections are most efficient at high angles of incidence and fail to reflect at shallow angles, for example normal to the surface. In order to achieve internal reflection, the angle of incidence should be greater than the critical angle. The critical angle is the angle below which light no longer reflects between a pair of materials.

Referring back to FIG. 2, for those embodiments of the present invention that utilize external reflection, a foil or some other highly reflective material can be utilized within the outer shell 212, chassis 35, or both. The highly reflective material, such as foil, can be disposed on the interior surface 375 of the outer shell 212 or the interior surface 377 of the chassis 35. In other embodiments, the highly reflective material, such as foil can be wrapped around the transmission element 33.

For those embodiments utilizing internal reflection, a material may be selected having high refractive index, for example above 1.0. For example, the material selected for the transmission element 33 may comprise a refractive index of greater than about 1.4, greater than about 1.5, greater than about 1.6, or less than about 1.7, less than about 1.6, less than about 1.5, or any number within the values provided or any ranges within the values provided. In some embodiments, the material selected for the transmission element 33 has a refractive index of between about 1.4 to about 1.6.

Figure 4A:
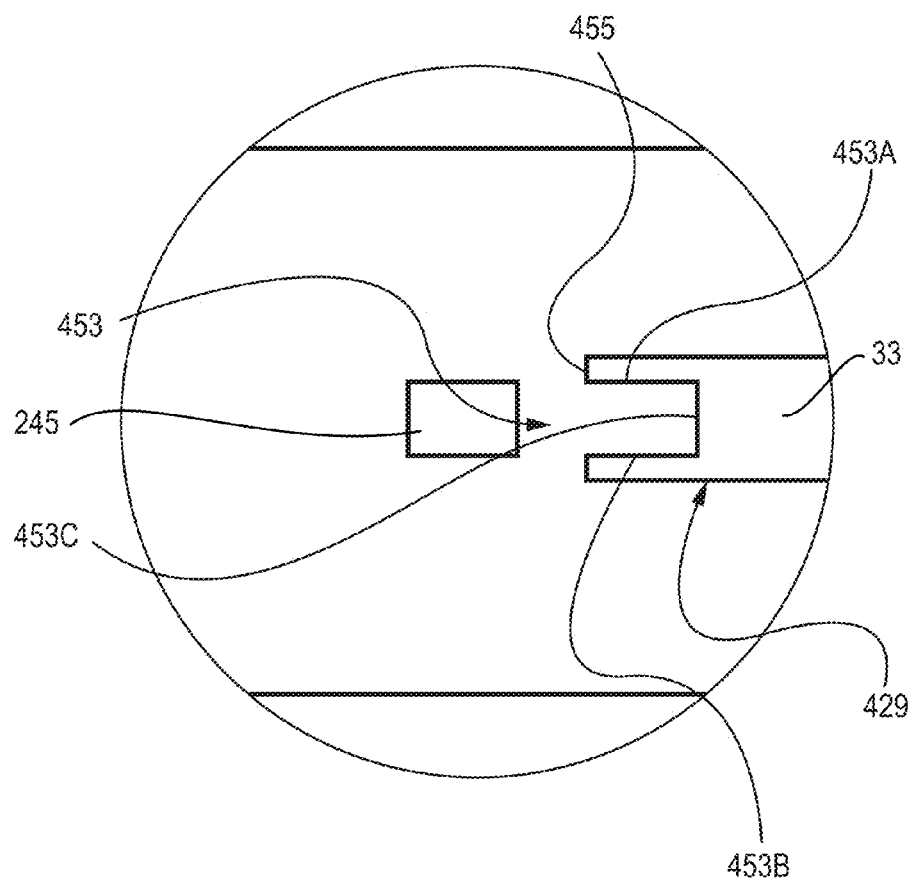
FIG. 4A is a close up view showing a portion of FIG. 3.
Figure 4B:
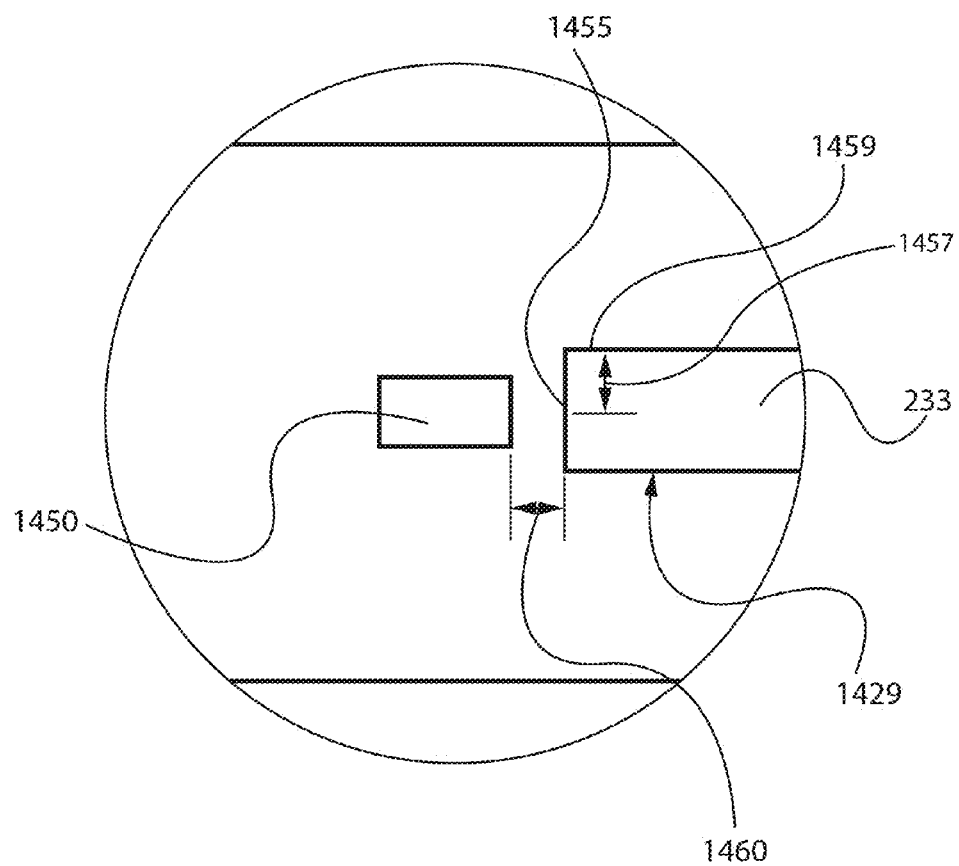
FIG. 4B is a close up view showing a portion of FIG. 3.

Referring to FIGS. 4A and 4B, in such embodiments, an outer surface 429, 1429, of the transmission element 33, 233, may be polished. The polished outer surface 429, 1429 of the transmission element 33, 233, can reduce the amount of leakage of light from the transmission element 33, 233.

In some embodiments, as shown in FIG. 4A, the transmission element 33 may comprise a receptacle 453 for receiving the output source 245, such as an LED. The receptacle 453 may be disposed on an end 455 of the transmission element 33. One benefit of providing a receptacle 453 on the end 455 of the transmission element 33 is that during manufacturing, the output source 245, such as an LED, may be inserted into the receptacle 453 thereby reducing the chance for misalignment of the output source 245 with respect to the transmission element 33. This can help reduce the amount of leakage of light between the output source 245 and the transmission element 33.

As stated previously, to achieve internal reflection, impinging light may be above the critical angle. The angle at which light impinges upon the transmission element 33 can be impacted by the distribution angle (discussed hereafter) of the output source 245 or 1450 (shown in FIG. 4B). For those output sources having a small distribution angle, the design of the receptacle 453, for example having sides 453A and 453B perpendicular to face 453C, may be sufficient to capture the majority of light emitted from the output source 245 for internal reflection. However, any light which is not above the critical angle will generally not be internally reflected. Accordingly, the sides 453A, 453B and/or the face 453C may be configured to increase the amount of light which is above the critical angle. For example, the sides 453A, 453B may be tapered toward or away from the face 453C. Similarly, the face 453C may include an angled surface, multiple angled surfaces, curved surfaces, for example lens shaped (convex or concave curvature), to increase the amount of emitted light which is above the critical angle.

Referring to FIG. 4B, in some embodiments, a transmission element 233 may be configured with a flat surface on an end 1455 as shown in FIG. 4B. In such embodiments, an output source 1450, such as an LED, may be positioned a distance 1460 away from the end 1455. In an effort to reduce the amount of light leaked from the output source 1450, distance B (1460) should generally be within the following guidelines.

$$B \le \frac{A}{\tan(\alpha)}$$

Where α is the half angle α available from a manufacturer's specifications for an output source of light, and where A (1457) is a leg of projection on the transmission element 233. The leg of projection 1457 is the straight line distance from the midpoint of the output source 1450 projected onto the transmission element 233 to an edge 1459 of the transmission element 233.

For those embodiments utilizing internal reflection, the distribution angle of the output source 245, 1450, such as an LED, should be considered. If the distribution angle is too broad, a portion of the light provided to the transmission element 33, 233 may not be internally reflected and instead will be leaked out of the transmission element 33, 233. Any suitable distribution angle may be utilized. Some examples of suitable distribution angles include greater than about 0 degrees, greater than about 1 degrees, greater than about 2 degrees, greater than about 5 degrees, greater than about 6 degrees, greater than about 8 degrees, greater than about 10 degrees, greater than about 12 degrees, greater than about 14 degrees, greater than about 16 degrees, greater than about 18 degrees, greater than about 20 degrees, greater than about 22 degrees, or less than about 22 degrees, less than about 20 degrees, less than about 18 degrees, less than about 16 degrees, less than about 14 degrees, less than about 12 degrees, less than about 10 degrees, less than about 8 degrees, or any number within the values provided or any ranges within the values provided.

Referring to FIG. 3A, as stated previously, a transmission element 33 can transmit electromagnetic energy, such as light from an output source 245 to the indication element 30. In an effort to reduce the amount of energy leaked through the transmission element 33, a reflective core 461 disposed in the transmission element 33 may be utilized. The reflective core 461 can reduce the amount of light which is lost through the transmission element 33 and transmission element ring 65 into the handle or neck of the brush. Additionally, the reflective core 461 can assist in distributing light through the indication element 30 to the outer lateral surfaces 87 of the indication element 30.

Figure 5:
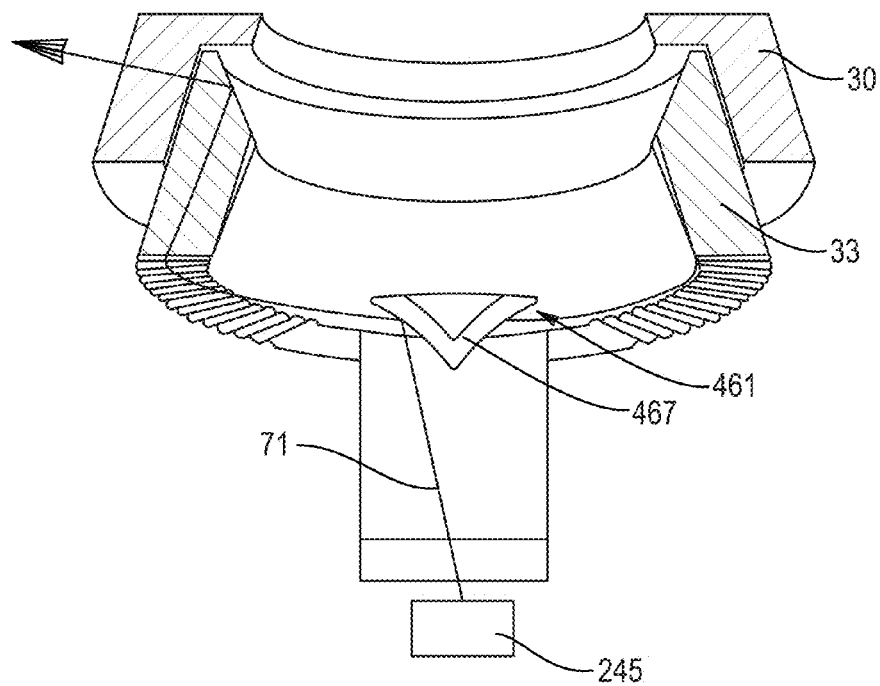
FIG. 5 is a cross-sectional view of an indicator mechanism according to one embodiment illustrated and described herein.

As shown in FIG. 5, the reflective core 461 may comprise one or more faces 467, which may be polished, disposed within the transmission element 33. The faces 467 can be configured to redirect light 71 transmitted through the transmission element to the indication element 30.

Figure 6A:
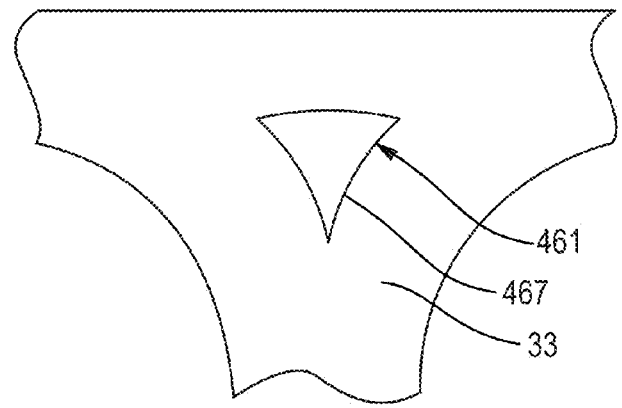
FIGS. 6A-6F are a close up views showing a portion of an indicator mechanism according one embodiment illustrated and described herein.
Figure 6B:
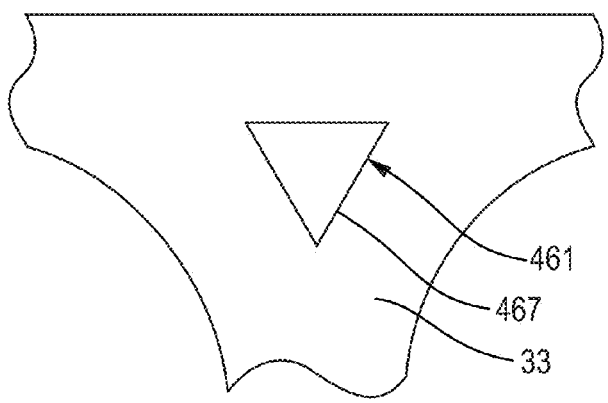
Figure 6C:
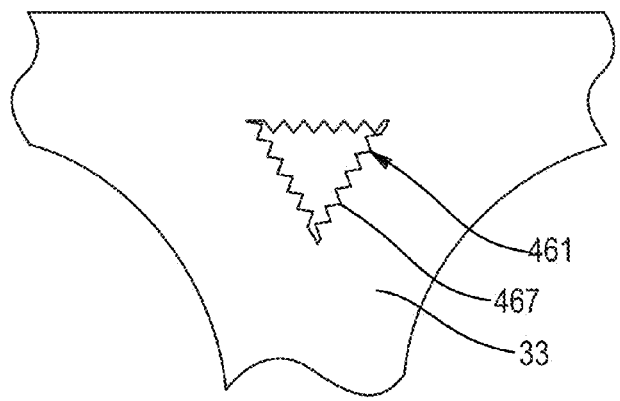
Figure 6D:
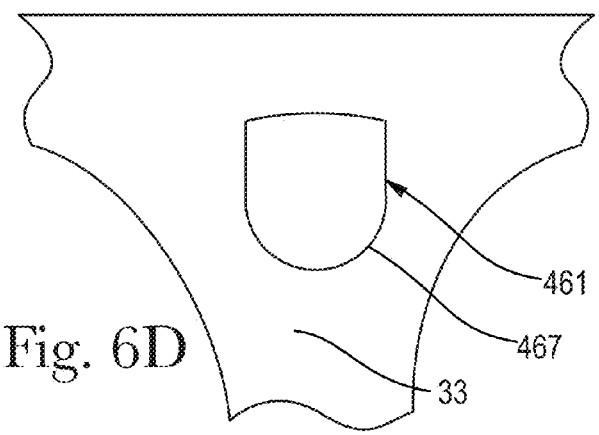
Figure 6E:
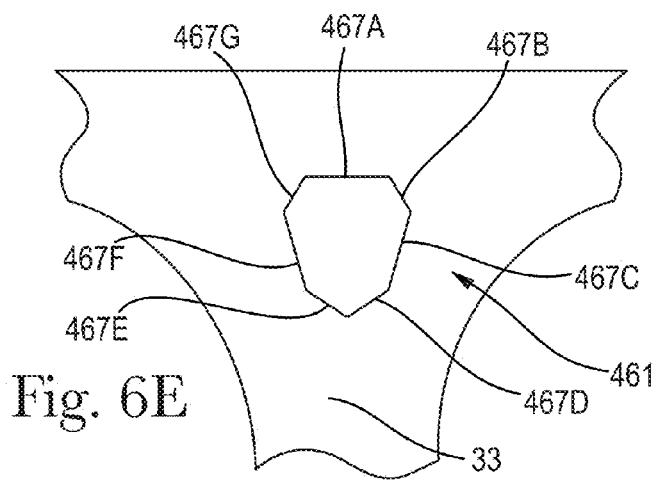
Figure 6F:
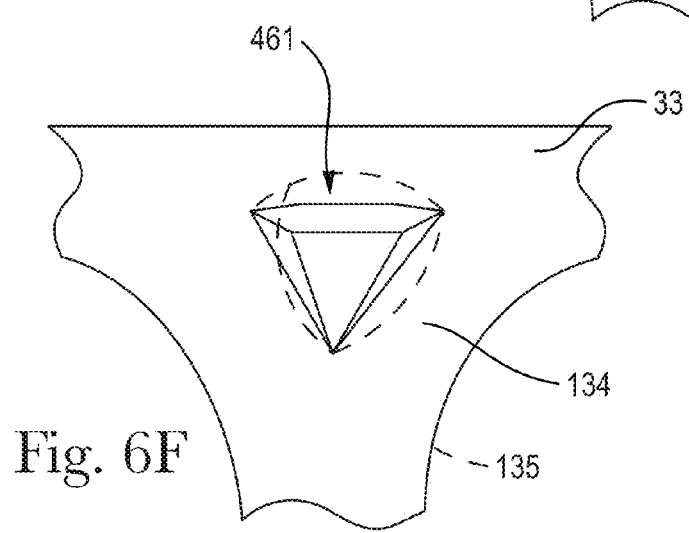
Figure 7:
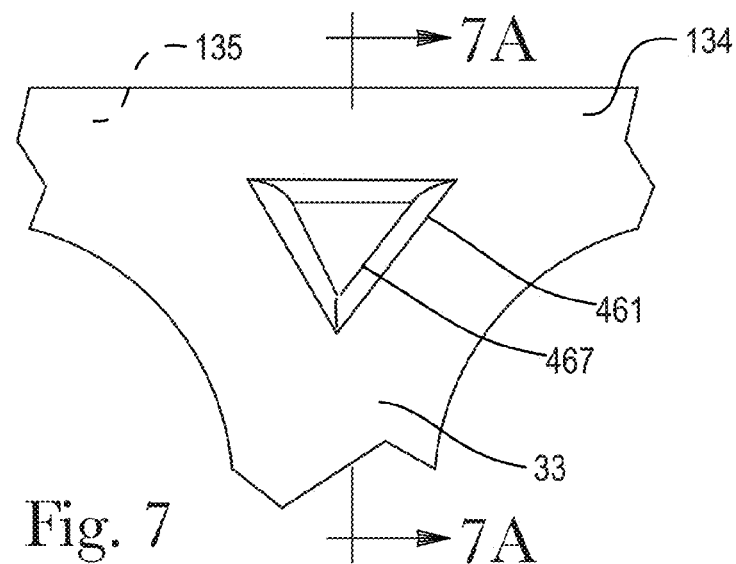
FIG. 7 is a close up view showing a portion of an indicator mechanism according to one embodiment illustrated and described herein.
Figure 7A:
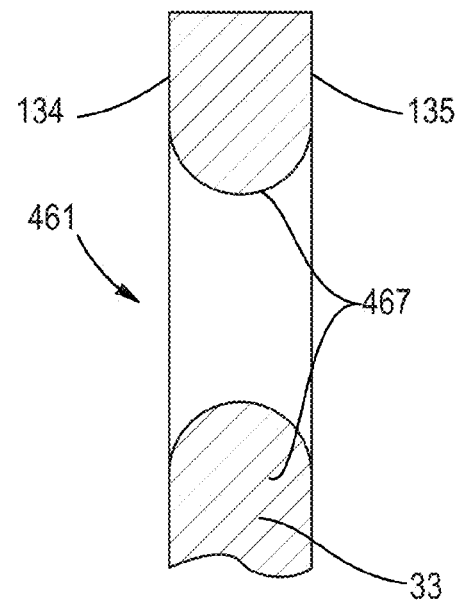
FIG. 7A is a cross-sectional view of the indicator mechanism portion of FIG. 7 along section line 7A-7A.
Figure 8:
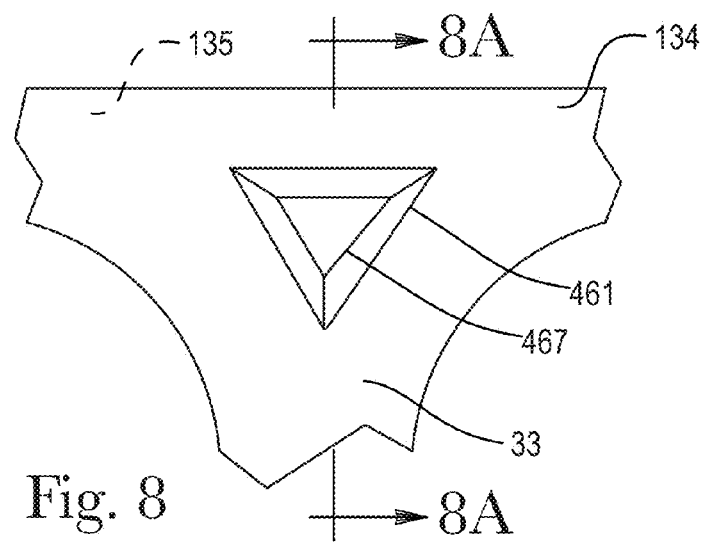
FIG. 8 is a close up view showing a portion of an indicator mechanism according to one embodiment illustrated and described herein.
Figure 8A:
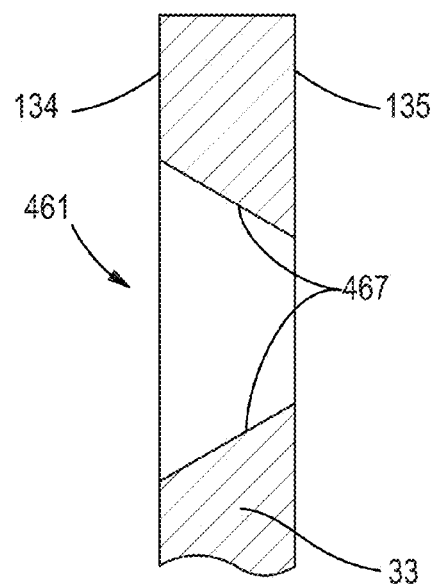
FIG. 8A is a cross-sectional view of the indicator mechanism portion of FIG. 8 along section line 8A-8A.

The faces 467 of the reflective core 461 may be configured in a wedge shape, or any other shape, such as a cone, that will facilitate the dispersion of electromagnetic energy, such as light, towards the indication element 30. The faces 467 of the reflective core 461 may be of any shape to facilitate dispersion of electromagnetic energy towards the indication element 30, for example, as shown in FIGS. 6A, 6B, 6C, along any portion of their length or along their entire length one or more of the faces 467 may be curved, straight, notched, U-shaped or any combination thereof. In addition to assist in the dispersion of electromagnetic energy to the indication element the reflective core may have any number of faces, as shown in FIG's 6D and 6E. For example, as shown in FIG. 6E the reflective core 461 has seven faces 467A, 467B, 467C, 467D, 467E, 467F, 467G. Further, as shown in FIG. 6F a transmission element 33 may also have a front side 134 and a back side 135 and the shape of the reflective core 461 on the front side 134 of the transmission element 33 can differ from the shape of the reflective core 461 on the backside 135 of the transmission element 33. In certain embodiments the reflective core 461 penetrates completely through the transmission element 33 to form a passageway from the front side 134 of the transmission element 33 to the back side 135 of the transmission element 33. In other embodiments the reflective core 461 does not completely penetrate the transmission element 33. In still other embodiments the reflective core 461 does not penetrate the transmission element 33 at all, but is instead integral with the transmission element 33, for example the reflective core 461 may comprise reflective surfaces embedded within the transmission element 33. Further in cross-section the faces of the reflective core may be angled, curved, or otherwise shaped to increase the reflection of light towards the indication element. For example, as shown in FIGS. 7 and 7A the faces 467 of the reflective core 461 may be curved in cross-section, while FIGS. 8 and 8A show the faces 467 are angled away from the front side 134 of the transmission element 33 towards the backside 135 of the transmission element 33.

Referring back to FIG. 5, the reflective core 461 as shown can be a recess which remains empty in the final product. In certain embodiments, the reflective core 461 may be partially filled with a material. Where the reflective core 461 is partially filled, an air gap between the filling material and the faces 467 may be provided. The existence of this air gap can ensure that internal reflection is maintained within the indication element 30. In some embodiments, the reflective core 461 may be completely filled with material which has a lower refractive index than that of the material of the reflective core.

It is believed that without the reflective core 461 less than about 10 percent of the light provided by the output source would be emitted by the indication element 30. And, it is believed that with the reflective core 461 about 90 percent or more of the light provided by the output source 245 would be emitted by the indication element 30. In certain embodiments, the light emitted by the indication element 30 is greater than about 10 percent of the light provided by the output source, greater than about 20 percent, greater than about 30 percent, greater than about 40 percent, greater than about 50 percent, greater than about 60 percent, greater than about 70 percent, greater than about 80 percent, greater than about 90 percent, less than about 100 percent, less than about 90 percent, less than about 80 percent, less than about 70 percent, less than about 60 percent, less than about 50 percent, less than about 40 percent, less than about 30 percent, less than about 20 percent, or any number within the values listed above or any ranges comprising and/or within the values above.

FIG. 9 shows electromagnetic energy, such as light 71, from an output source 245, such as an LED, travels along the transmission element 33 towards the indication element 30. In certain embodiments at least a portion of the light travelling towards the indication element 30 along the transmission element 33 is reflected off of the faces 467 of the reflective core 461 back towards the transmission element 33. This light is redirected towards the bottom edge 67 of the transmission element ring 65. In certain embodiments to produce a constant light distribution all around the circumference of the indication element 30, the reflective core 461 redirects the light beams 71 that are coming from the output source 245 through the transmission element 33, in such a manner that a constant density of light beams 71 are achieved on the bottom edge 67 of the transmission element ring 65. By choosing the right angle and shape (for example curved) of the reflective core an expansion of the light can be realized—through the production of a constant light density on the bottom edge 67. For illustration purposes FIG. 9A, which is a depiction of FIG. 9 having a lateral cut through the transmission element 33, and the resulting transmission element 33 and transmission element ring 65 opened up and flattened out, shows how the reflective core 461 distributes light beams 71 around the circumference of the transmission element ring 65.

The bottom edge 67 of the transmission element ring 65 has a reflective surface to further redirect the light towards the indication element 30. The reflective surface of the transmission element ring can be coated with a reflective material or as shown in FIG. 9 can be comprised of surface contours 83 that are formed in such a manner to redirect the light towards the indication element 30, or both reflective coatings and surface contours can be used.

Figure 9B:
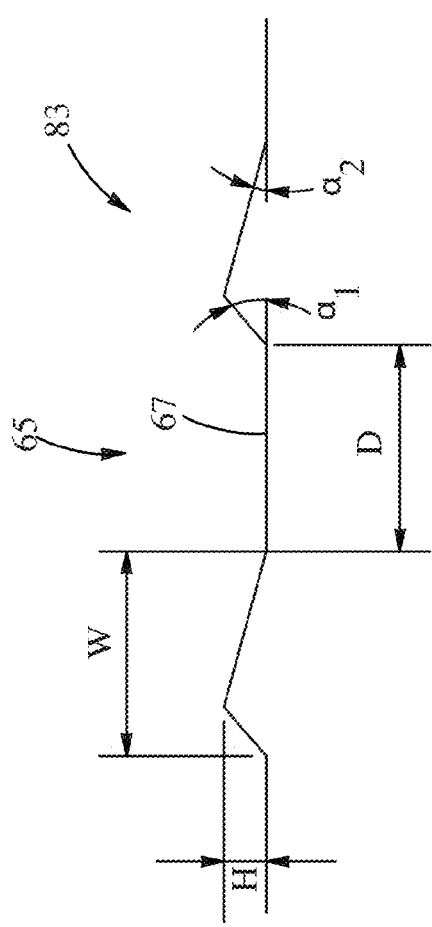
FIG. 9B is a close up view showing a portion of a transmission element ring according to one embodiment illustrated and described herein.
Figure 9C:
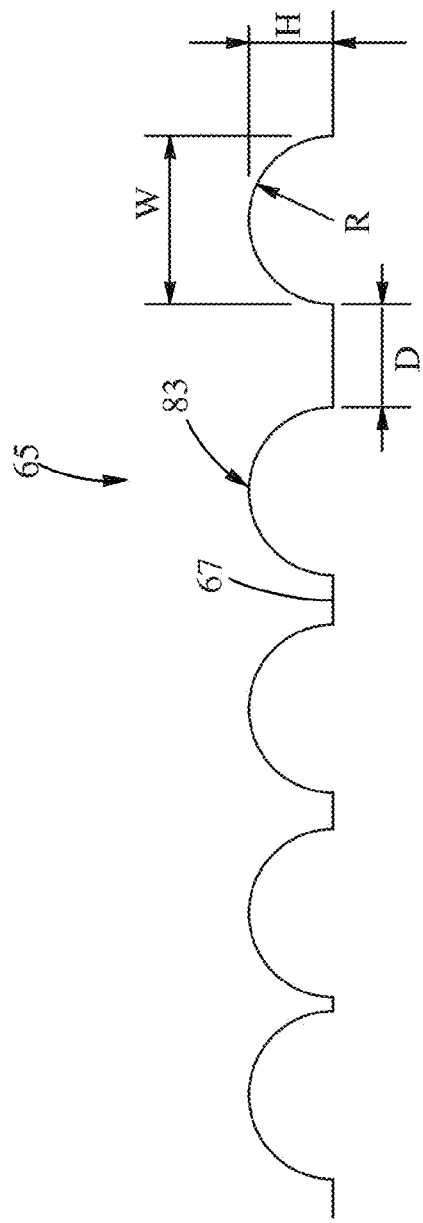
FIG. 9C is a close up view showing a portion of a transmission element ring according to one embodiment illustrated and described herein.

FIG. 9 shows a series of surface contours 83, in this instance in the shape of reflective teeth, which comprise two angled sides to produce a triangular protrusion. In certain embodiments, as shown in FIG. 9B to substantially use internal reflection, the surface contours have an orientation (angle $\alpha 1$ and $\alpha 2$) such that the light contacts the surface of a surface contour 83 on an angle below the critical angle. Further, in certain embodiments the angles ($\alpha 1$ and $\alpha 2$) may change depending on the position of the surface contour on the transmission element ring 65, for example the angles could change depending on the distance from the reflective core. The angle of $\alpha 1$ and $\alpha 2$ may be in the range of 0-45°. FIG. 9C shows that in addition to triangular surface contours, arched surface contours can be used, which can expand the light to create a more homogenous light distribution on the indication element. In certain embodiments, surface contours may have the following dimensions of height (H); width (W); and distance between adjacent surface contours (D):

$$H \leq W/2$$

$$D \geq 0$$

The height H of a surface contour may be $H \leq 3$ mm, for example in certain embodiments, 0.5 mm$\leq H \leq 1$ mm. Further, the position of the surface contour on the transmission element ring may affect the H, W, or D.

As shown in FIG. 9 the redirection of the light due to the surface contours 83 of the bottom edge 67 of the transmission element ring 65 allows light to be emitted from all outer lateral surfaces 87 of the indication element 30 providing an all around 360° effect. In certain embodiments, near the reflective core 461 where the light has a high intensity, less surface contours 83 can be used, while further away from the reflective core 461, such as at the backside 101, where the light intensity is already reduced, more surface contours 83 can be used to achieve a similar light intensity along the indication element 30. Otherwise, the indication element 30 may appear much brighter near the reflective core 461/output source 245 and much darker at areas further away from the reflective core 461/output source 245.

In certain embodiments, as shown in FIGS. 9D and 9E, the transmission element 33 may be non-linear along its length, such that the transmission element 33 might contain one or more angles, or as shown in FIGS. 9D and 9E, one or more curves. Such an orientation of the transmission element 33 is beneficial in certain embodiments, when for example as in a powered toothbrush there may be obstructions, such as motors or batteries, between the output source and the indication element. Therefore, the non-linear orientation of the transmission element 33 allows for the transfer of light to the transmission element ring 65 and indication element 30 from the output source 245 even when a direct path is obstructed. The transmission element may also connect to the transmission element ring at any point along the transmission element ring that allows for the transmission of light from the transmission element. In addition, the surface contours may be present on any surface or surfaces of the transmission element ring. For example as shown in FIG. 9E the surface contours 83 are positioned on the inner surface of the transmission element ring 65, such that the light is reflected outwards towards the indication element 30, which in this embodiment is positioned at least partially along the outer periphery 66 of the transmission element ring 65. FIGS. 9D and 9E also demonstrate that a reflective core is not present in certain embodiments, as the transmission element 33 and transmission element ring 65 are able to distribute the light to the indication element.

Figure 10:
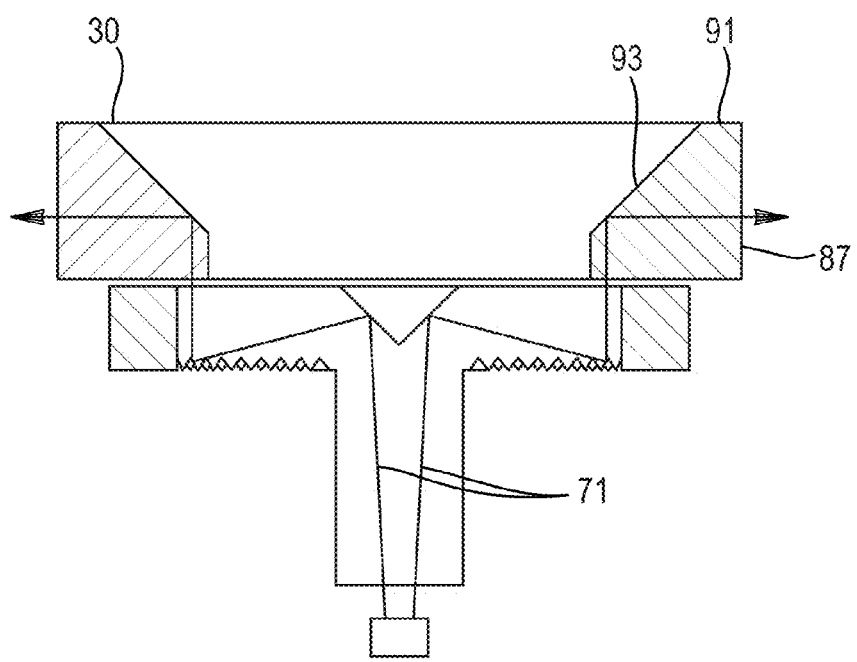
FIG. 10 is a cross-sectional view of an indicator mechanism according to one embodiment illustrated and described herein.

With reference back to FIG. 9 the redirected light from the bottom edge 67 of the transmission element ring 65 enters the indication element 30 where it is directed towards the outer lateral surface 87 of the indication element 30 or in certain embodiments would be reflected off a surface of the indication element 30, for example the top surface 91 or inner surface 93, which may be coated with a reflective material. In certain embodiments, as shown in FIG. 10, the top surface 91, inner surface 93, or both may be formed in a manner to redirect light 71 towards the outer lateral surface 87 of the indication element 30, for example the top surface 91 or inner surface 93 may be curved or in the case of the embodiment shown in FIG. 10 the surfaces may be angled.

Additionally, embodiments comprising multiple output sources are contemplated. For example, a receptacle may be configured such that two LEDs may be positioned therein. In certain embodiments where an LED provides a signal a first LED may provide a first output signal for one condition, for example brushing time, while a second LED may provide a second output signal for a second condition, for example time for brush replacement, wherein the first output signal and the second output signal are different. Similarly, in embodiments where the transmission element does not include a receptacle, a plurality of output sources, for example LEDs, may be utilized.

Figure 11A:
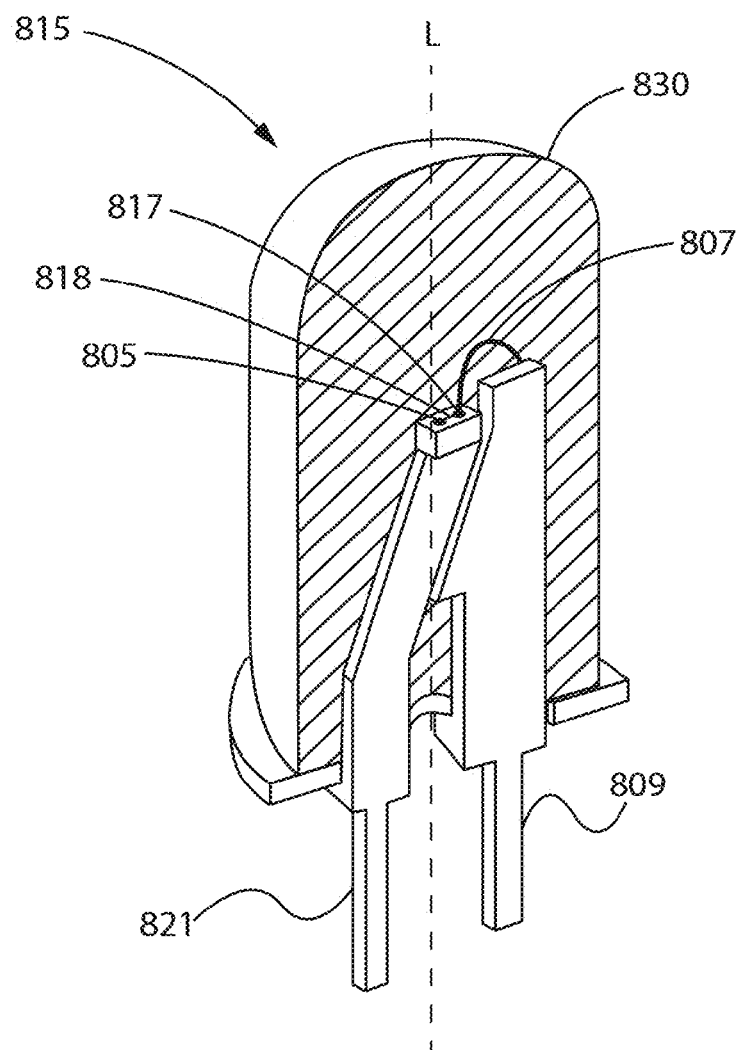
FIGS. 11A-11D are cross sectional views of exemplary LEDs which are suitable for use with the oral hygiene implement of the present disclosure.

In addition, certain embodiments are also contemplated where the output source comprises an LED having multiple dices as described in U.S. Patent Application Publication No. 2005/0053896A1. As shown in FIG. 11A, an LED 815 may include a lens 830, and one positive lead 821 and one negative lead 809. The LED 815 may comprise more than one light emitter and more than one semi-conductor substrate, and can have more than two leads. Embodiments are contemplated where the LED comprises two dices. Additionally, embodiments are contemplated where the LED comprises more than two dices.

For example, the LED 815 may comprise multiple light emitting dices 805 and 817 and a wire bonding 807 and 818. The wire bonding 818 may serve as the connection between the dices 805 and 817. This connection can be either a parallel connection or a serial connection.

Figure 11B:
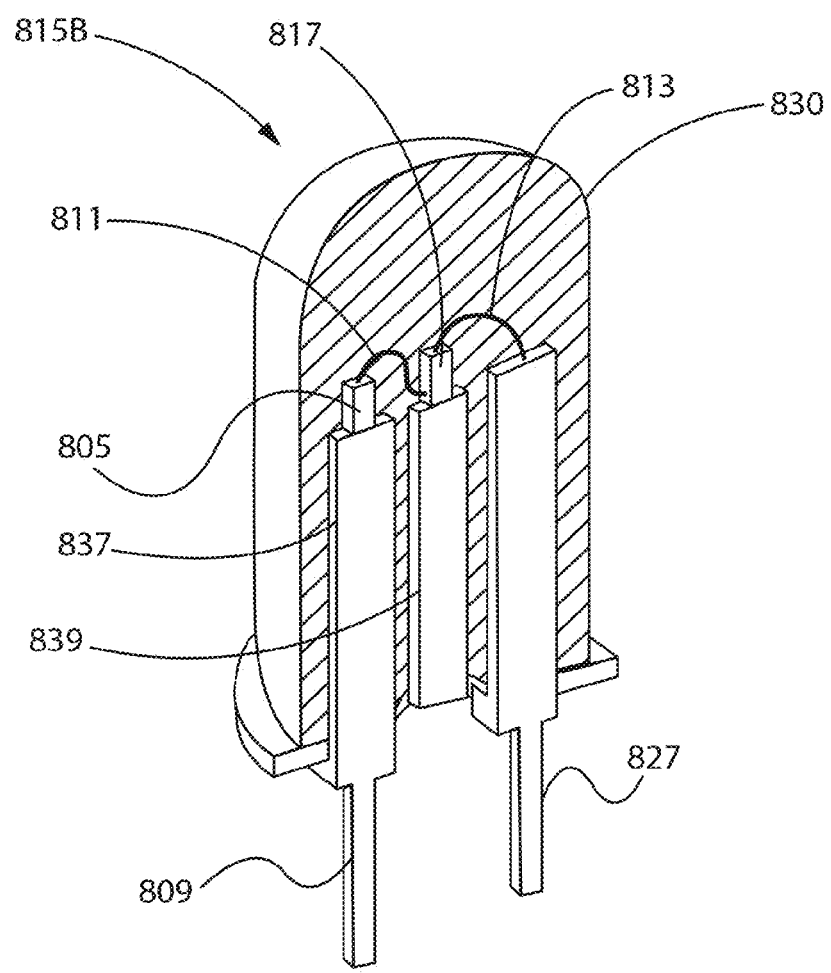

As shown in FIG. 11B, an LED 815B (two wire LED) may comprise multiple dices 805 and 817 connected in series. The LED 815B may include one positive lead 809 and one negative lead 827. As shown, each dice 805 and 817 may have an individual pedestal 837 and 839. The dices have a serial connection 811 connecting the top of dices 805 to the bottom of dices 817, and wire bonding 813 connects the top of dices 817 to the negative lead 827. All light from the light emitting sources may be combined to result in a single light output at lens 830 of LED 815B.

Figure 11C:
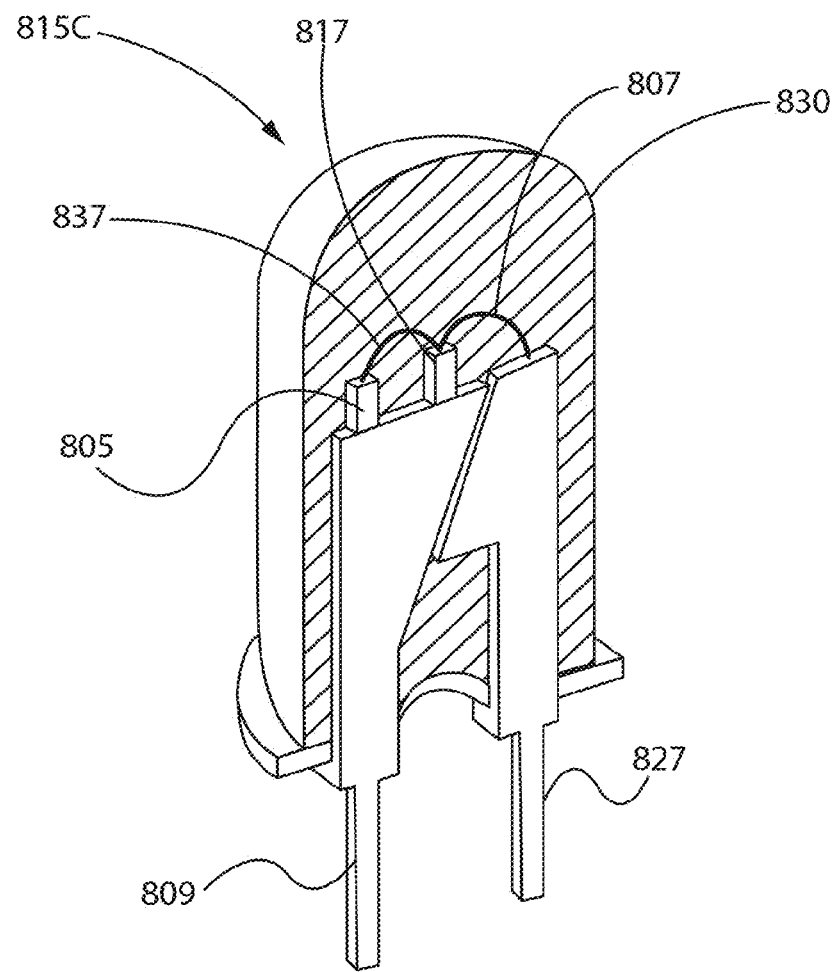

As shown in FIG. 11C, an LED 815C may include multiple dices 805 and 817 connected in parallel. The LED 815C may comprise a single light output, the lens 830, and one positive lead 809, and one negative lead 827. The dices may have a parallel connection, wire bonding 837 connecting the top of dices 805 to the top of dices 817, and wire bonding 807 connecting the top of dices 817 to the top of the common negative lead 827. All light from the light emitting sources can be combined to result in a single light output at lens 830 of LED 815C.

Figure 11D:
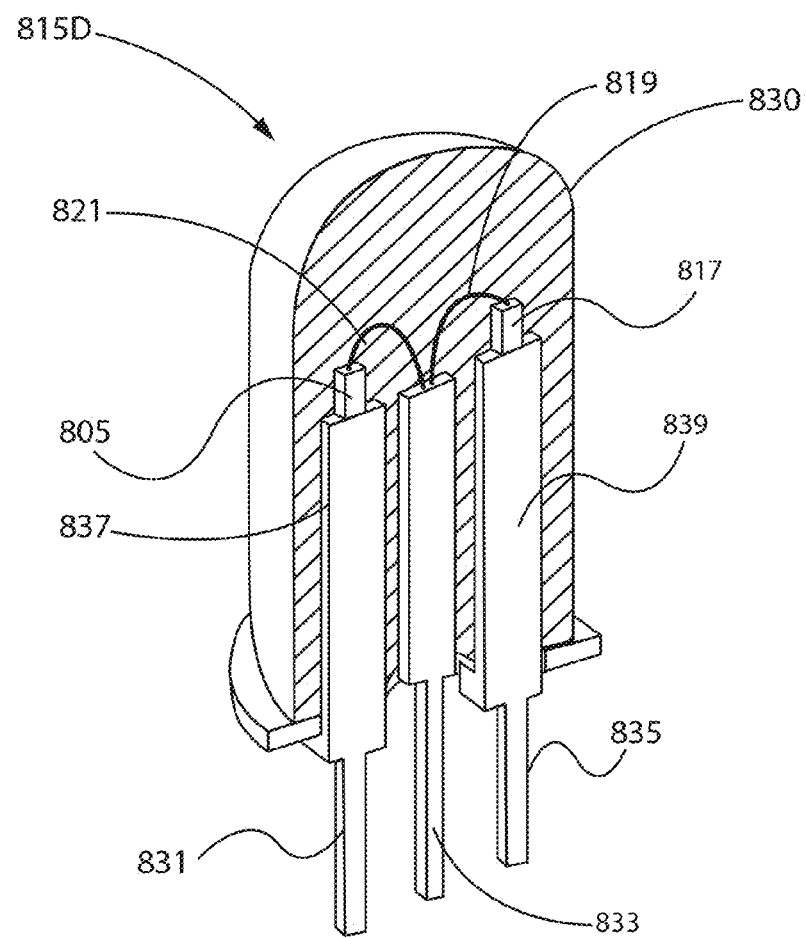

As shown in FIG. 11D, an LED 815D (three wire LED) may include multiple dices 805 and 817. The LED 815D may comprise a lens 830, two semiconductor substrates, dices 805 and 817 shown connected in parallel, wire bondings 819 and 821, one positive lead 833, and two negative leads 831 and 835. This LED 815D also emits light from a single light output, the lens 830. Each dice may have an individual pedestal 837 and 839. It is also contemplated that the LED 815D can comprise two positive leads, and one negative lead; and the dices 805 and 817 can be connected in series.

Additionally, the LED can comprise more than two semiconductor substrates having light emitting properties, and the LED can comprise more than two leads. The LED can have a common or shared lead, or can have individual leads for each semi-conductor substrate having light emitting properties. Further, each semi-conductor substrate having light emitting properties can be individually powered by a separate power source, such as a battery.

One advantage of a three wire LED, for example LED 815D, is that the dices 805 and 817 may be independently operated. For example, where the LED 815D comprises two positive leads, the dices may be independently controlled. So, the first dice 805 may be operated at eighty percent capacity while the second dice 807 is operated at twenty percent capacity. As another example, the first dice 805 may be operated at fifty percent while the second dice 817 is operated at 100 percent. There are countless combinations for operating levels of the first dice 805 and the second dice 817. It is believed that such combinations can achieve color blends which create a unique visual effect for the user.

For two wire LEDs light blends are also possible. For example, the polarity of the supply voltage can be switched at a high enough rate, for example higher than 70 Hz, such that the dices can be driven and create a blended color effect. When the polarity of the supply voltage is in a first state, a first dice may be energized. When the polarity of the supply voltage is in a second state, a second dice may be energized. If the polarity of the supply voltage is switched fast enough, a user may perceive a color blend. The switching rate of the polarity of the supply voltage may be greater than about 70 Hz, greater than about 80 Hz, greater than about 90 Hz, greater than about 100 Hz, greater than about 110 Hz, greater than about 120 Hz, greater than about 130 Hz, less than about 130 Hz, less than about 120 Hz, less than about 110 Hz, less than about 100 Hz, less than about 90 Hz, or any number within the values provided or any ranges within the values provided.

As stated above, these dices can be electrically connected in parallel or in series. When they are connected in series, all current considerations are the same as for one single dice. The total voltage can be approximated by the equation below:

$$V = V_{f1} + V_{f2} + \ldots + V_{fn}$$

where n is equal to the number of dices and $V_f$=forward voltage for a particular dice. If the dices are connected in parallel, the total voltage is approximately that of a single dice.

Serial connection works well because it adjusts for differences between the dices. When the dices are connected in series, they automatically adjust their forward voltages and their luminous intensity become very close. In either arrangement the two dices have approximately the luminous intensity of $1.6 \times P_i$, where $P_i$ is luminous intensity of a single dice. A three dices LED will likely have the luminous intensity of about $2.26 \times P_i$. (Interference between the dices can prevent the luminous intensity calculation from being a multiplier by the number of dice.) These dices can deliver the same color of light, or they can have different colors of light. However, if each individual light emitter emits the same light, the luminous intensity of that color light from that one single LED is greater than a single standard LED emitting light of one color.

A single LED could also contain two dices emitting different colors of light, for example a wavelength selected from the range of greater than about 370, 380, 390, 400, 425, 440, 450, 475, 500, 600, 700, 800, 900, or 1,000 nanometers. The dices could also be selected such that the dices emit light of a different wavelength within the same color range; for example the dices could emit light having different wavelengths that result in the color blue. Further, the combination of the different wavelengths of light at the single optical output of the LED (the lens) could result in a specific combination of colors that delivers an oral care benefit. Some colors are difficult to achieve by a single wavelength of light; this invention can be used to produce light of one of these unique colors. Thus the combination of different colors at the single optical output may result in a color that cannot be achieved by one dice alone.

For those embodiments comprising multiple LEDs or an LED with multiple dices, the oral hygiene implement of the present invention may provide the user with multiple signals. For example, a first dice may be energized providing the user with a first visual indication. The first visual indication may correlate to a predetermined amount of time brushed by the user, for example. A second dice may be energized providing the user with a second visual indication. The second visual indication may signal the user that it is time to replace the oral care device. In such embodiments, the first visual indication may comprise first color while the second visual indication comprises a second color which is different than the first color. Any suitable colors may be utilized.

Toothbrushes constructed in accordance with the present disclosure may provide feedback to the user via the indication element for a variety of conditions. For example, during a brushing session, a visible signal may be provided when the user has brushed their teeth for a predetermined amount of time, for example two minutes, three minutes, etc. As another example, a visible signal may be provided to the user regarding when the brush should be replaced. As yet another example, a visible signal may be provided to the user regarding the time the user has brushed over a number of brushing routines. As another example, a visible signal may be provided to the user when too much force is applied to the brush head and therewith a chance is given that the user can damage his gums. In such embodiments, a first signal may be provided where the user has successfully brushed for a requisite period of time, for example two minutes, for a predetermined number of brushing routines. A second signal may be provided to the user where the user has not brushes the requisite time for each and every of the predetermined number of brushing routines. Further signals may be sent from the toothbrush, for example by using light in the infrared spectrum, such as wavelengths of around 950 nanometers. The indicator element can distribute the infrared signal in all directions to assure that a receiver can receive signals even if the toothbrush is hold in various positions.

The signal provided to the user may be constant, for example provide a signal to the user during the entire brushing routine. Alternatively, the signal provided to the user can be provided at the end of the brushing routine. For example, where the user has not brushed for the predetermined amount of time, for example two minutes, in a previous brushing routine, the signal provided to the user may flash red or show a red visible signal for a predetermined time period during a subsequent brushing routine. As another example, where the user brushed for a predetermined amount of time during a previous brushing routine, the signal provided to the user may flash green or show a green visible signal for a predetermined period of time.

In other embodiments, the signal can be provided to the user intermittently during the brushing routine. For example, the signal can be provided to the user on predetermined time intervals. For example, a signal may be provided to the user every 20 seconds. Any suitable time interval can be selected. For example, the time interval between signals can be greater than about 0.1 second, greater than about 0.2 seconds, greater than about 0.3 seconds, greater than about 0.4 seconds, greater than about 0.5 seconds, greater than about 0.6 seconds, greater than about 0.7 seconds, greater than about 0.8 seconds, greater than about 0.9 seconds, greater than about 1 second, greater than about 2 seconds, greater than about 3 seconds, greater than about 4 seconds, greater than about 5 seconds, greater than about 6 seconds, greater than about 10 seconds, greater than about 15 seconds, greater than about 20 seconds, greater than about 25 seconds, greater than about 30 seconds, greater than about 40 seconds, greater than about 50 seconds, greater than about 60 seconds, and/or less than about 60 seconds, less than about 50 seconds, less than about 40 seconds, less than about 30 seconds, less than about 25 seconds, less than about 20 seconds, less than about 15 seconds, less than about 10 seconds, less than about 5 seconds, less than about 4 seconds, less than about 3 seconds, less than about 2 seconds, less than about 1.5 seconds, less than about 1, less than about 0.9 seconds, less than about 0.8 seconds, less than about 0.7 seconds, less than about 0.6 seconds, less than about 0.5 seconds, less than about 0.4 seconds, less than about 0.2 seconds, or less than about 0.1 seconds.

Previously, a time interval between signals was discussed. In some embodiments, a processor may be configured to modify the time interval between the signals provided to the user either during a particular brushing routine or over a series of brushing routines. For example, during a first brushing routine, if the user brushes for a predetermined amount of time, for example two minutes, the interval between signals to the user may be at a first time interval. If in a second brushing routine, the user does not brush for the predetermined amount of time, the signals to the user may be at a second time interval. In such an embodiment, the first time interval may be greater than the second time interval thereby providing more feedback to the user. In some embodiments, the time intervals may be switched such that the user is provided more feedback for brushing the predetermined amount of time.

In regard to the materials making up the toothbrush the outer shell 212 may be any suitable material. Some examples of suitable materials include polypropylene, ABS (acrylonitrile-butadiene-styrene copolymer), ASA (acrylonitrile-styrene-acrylate), copolyester, POM (polyaformaldeyde), combinations thereof, and the like. Additional suitable materials include polypropylene, nylon, high density polyethylene, other moldable stable polymers, the like, and/or combinations thereof. In some embodiments, the handle, the neck, and/or the head, may be formed from a first material and include recesses, channels, grooves, for receiving a second material which is different from the first. For example, the handle may include an elastomeric grip feature or a plurality of elastomeric grip features. The elastomers among the plurality of elastomeric grip features may be similar materials or may be different materials, for example color, hardness, combinations thereof or the like.

The sealing element 270 may comprise any suitable material. Some examples of suitable material include thermoplastic elastomers, silicone based materials, NBR (nitrile butadiene rubber), EPDM (ethylene propylene diene monomer), Viton™, etc.

In some embodiments, recycled and/or plant derived plastics may be utilized. For example, PET (polyethylene terephthalate) may be utilized in some embodiments. The PET may be bio based. For example, the PET may comprise from about 25 to about 75 weight percent of a terephthalate component and from about 20 to about 50 weight percent of a diol component, wherein at least about one weight percent of at least one of the terephthalate and/or the diol component is derived from at least one bio-based material. Similarly, the terephthalate component may be derived from a bio based material. Some examples of suitable bio based materials include but are not limited to corn, sugarcane, beet, potato, starch, citrus fruit, woody plant, cellulosic lignin, plant oil, natural fiber, oily wood feedstock, and a combination thereof.

Some of the specific components of the PET may be bio based. For example, monoethylene glycol and terephthalic acid may be formed from bio based materials. The formation of bio based PET and its manufacture are described in United States Patent Application Publication Nos. 20090246430A1 and 20100028512A1.

As mentioned previously, in certain embodiments for example as shown in FIGS. 1 and 2, the toothbrush 10 may include a replaceable head 14, neck 16 or both. Specifically, the head 14 may be removable from the neck 16 and/or the neck 16 may be removable from the handle 12. Herein, whether the head 14 is removable from the neck 16 or the neck 16 is removable from the handle 12, such replaceable elements will be termed "refills". In such embodiments, the processor may be programmed with a plurality of algorithms in order to establish a time period for cumulative use of a particular refill and/or for identification of a particular use. Some suitable examples of oral care implements which can recognize a particular refill are described in U.S. Pat. Nos. 7,086,111; 7,207,080; and 7,024,717.

The interconnectivity between the neck 16 and the handle region 12 can be provided in any suitable manner. Some suitable embodiments are discussed with regard to U.S. Pat. Nos. 7,086,111, 7,207,080, and 7,024,717.

The toothbrush of the present invention may further comprise a power source as discussed previously. The power source may be any suitable element which can provide power to the toothbrush. A suitable example includes one or more batteries that may be sized in order to minimize the amount of real estate required inside the toothbrush. For example, where the output source consists of a light emitting element the power source may be sized relatively small, for example smaller than a triple A battery. The battery may be rechargeable or may be disposable. In some embodiments, the power source may include alternating current power as provided by a utility company to a residence. Other suitable power sources are described in U.S. patent application Ser. No. 12/102,881, filed on Apr. 15, 2008, and entitled, "Personal Care Products and Methods".

In some embodiments, a user operated switch may be provided which can allow the user to control when timing indication begins. The switch may be in electrical communication with the power source and the output signal element and/or the timer.

The elastomeric grip features of the handle may be utilized to overmold, at least in part, a portion of the timer, output signaling element, processor, cap, and/or power source. In such embodiments, these components may be in electrical communication via wiring which can similarly be overmolded. The elastomeric grip features may include portions which are positioned for gripping by the palm of the user and/or portions which are positioned for gripping by the thumb and index finger of the user. These elastomeric grip features may be composed of the same material or may be different, for example color, shape, composition, hardness, the like, and/or combinations thereof.

Additionally, as used herein, the term "contact elements" is used to refer to any suitable element which can be inserted into the oral cavity. Some suitable elements include bristle tufts, elastomeric massage elements, elastomeric cleaning elements, massage elements, tongue cleaners, soft tissue cleaners, hard surface cleaners, combinations thereof, and the like. The head may comprise a variety of contact elements. For example, the head may comprise bristles, abrasive elastomeric elements, elastomeric elements in a particular orientation or arrangement, for example pivoting fins, prophy cups, or the like. Some suitable examples of elastomeric cleaning elements and/or massaging elements are described in U.S. Patent Application Publication Nos. 2007/0251040; 2004/0154112; 2006/0272112; and in U.S. Pat. Nos. 6,553,604; 6,151,745. The cleaning elements may be tapered, notched, crimped, dimpled, or the like. Some suitable examples of these cleaning elements and/or massaging elements are described in U.S. Pat. Nos. 6,151,745; 6,058,541; 5,268,005; 5,313,909; 4,802,255; 6,018,840; 5,836,769; 5,722,106; 6,475,553; and U.S. Patent Application Publication No. 2006/0080794.

The contact elements may be attached to the head in any suitable manner. Conventional methods include stapling, anchor free tufting, and injection mold tufting. For those contact elements that comprise an elastomer, these elements may be formed integral with one another, for example having an integral base portion and extending outward therefrom. The head may comprise a soft tissue cleanser constructed of any suitable material. Some examples of suitable material include elastomeric materials; polypropylene, polyethylene, etc; the like, and/or combinations thereof. The soft tissue cleanser may comprise any suitable soft tissue cleansing elements. Some examples of such elements as well as configurations of soft tissues cleansers on a toothbrush are described in U.S. Patent Application Nos. 2006/0010628; 2005/0166344; 2005/0210612; 2006/0195995; 2008/0189888; 2006/0052806; 2004/0255416; 2005/0000049; 2005/0038461; 2004/0134007; 2006/0026784; 20070049956; 2008/0244849; 2005/0000043; 2007/140959; and U.S. Pat. Nos. 5,980,542; 6,402,768; and 6,102,923.

For those embodiments which include an elastomeric element on a first side of the head and an elastomeric element on a second side of the head (opposite the first), the elastomeric elements may be integrally formed via channels or gaps which extend through the material of the head. These channels or gaps can allow elastomeric material to flow through the head during an injection molding process such that both the elastomeric elements of the first side and the second side may be formed in one injection molding step.

As mentioned above, consumers prefer oral hygiene implements which can provide the consumer with an indication means that is visible during use. One way to increase the visibility of the indication means is to enhance the light distribution emanating from the indicating element. One way to compare indicating elements from various oral hygiene implements is to calculate a Total Visible Projected Angle ($\phi_T$) utilizing the equation: ($\phi_T$)=($\phi_1+\phi_2$).

In one embodiment, oral hygiene implements according to the present disclosure may have Total Visible Projected Angle ($\phi_T$) of greater than about 300 degrees. In another embodiment, oral hygiene implements may have a Total Visible Projected Angle ($\phi_T$) of greater than about 320 degrees and in another embodiment of greater than about 340 degrees. In another embodiment, oral hygiene implements may have a Total Visible Projected Angle ($\phi_T$) of from about 300 degrees to about 360 degrees. In another embodiment, Visible Projected Angle ($\phi_1$) is greater than about 130 degrees; in another embodiment greater than about 140 degrees; in another embodiment greater than about 150 degrees; in another embodiment greater than about 160 degrees; in another embodiment greater than about 170 degrees; and in yet another embodiment about 180 degrees. In another embodiment, Visible Projected Angle ($\phi_2$) is greater than about 130 degrees; in another embodiment greater than about 140 degrees; in another embodiment greater than about 150 degrees; in another embodiment greater than about 160 degrees; in another embodiment greater than about 170 degrees; and in yet another embodiment about 180 degrees.

In one embodiment, indication element 30 may exhibit a luminance of from about 1 cd/m$^2$ to about 5 cd/m$^2$; in another embodiment a luminance of at least about 1 cd/m$^2$; in another embodiment a luminance of at least about 2 cd/m$^2$; in yet another embodiment a luminance of at least about 3 cd/m$^2$; and in another embodiment a luminance of at least about 4 cd/m$^2$.

EXAMPLES

The following Examples provide a comparison between a Total Visible Projected Angle ($\phi_T$) for commercially available oral hygiene implements having an indication element to a Total Visible Projected Angle ($\phi_T$) for oral hygiene implements according to the present disclosure.

TABLE 1

Sample Oral Hygiene Implements Having An Indication Element

| Example | $\Phi_1$ | $\Phi_2$ | Total Visible Projected Angle ($\phi_T$) |
|---|---|---|---|
| 1. | 115 | 180 | 295 |
| 2. | 110 | 180 | 290 |
| 3. | 140 | 0 | 140 |
| 4. | 180° (±2°) | 180° (±2°) | 360° (±4°) |

*The results of Table 1 are shown in FIGS. 16A to 19

TABLE 1-continued

Sample Oral Hygiene Implements Having An Indication Element

| Example | $\Phi_1$ | $\Phi_2$ | Total Visible Projected Angle ($\phi_T$) |
|---|---|---|---|

Example 1 is a commercially available O/R toothbrush sold by The Procter and Gamble Company under the trademark Oral-B Professional Care 3000.
Example 2 is a commercially available O/R toothbrush sold by The Procter and Gamble Company under the trademark Oral-B Triumph 4000.
Example 3 is a commercially available powered toothbrush sold by Panasonic Corporation under the trademark Panasonic EW-DE 20.
Example 4 is an embodiment of a powered toothbrush in accordance with the present disclosure.

Test Methods

The test methods and apparatus described below may be useful in testing embodiments of the present disclosure:

Total Visible Projected Angle ($\phi_T$)

The Total Visible Projected Angle ($\phi_T$) is determined as follows:

Equipment

LMK 98-4 Color luminance measuring color camera and LMK Labsoft software. The color camera and software are available from TechnoTeam Bildverarbeitung GmbH, D-98693 Ilmenau GERMANY Base Plate Toothbrush Holder Camera Stand Half Cone and Half Cone Support Stand Computer with Monitor Definitions Total Visible Projected Angle ($\phi_T$)=($\phi_1+\phi_2$) where $\phi_1$ corresponds to front-facing surface of an oral hygiene implement oriented towards the half cone and $\phi_2$ corresponds to back-facing surface of an oral hygiene implement oriented towards the half cone.

Test Procedure

Obtain an oral hygiene implement, for example, a toothbrush including an indication element.

Remove any contact elements on the brush head.

Figure 12:
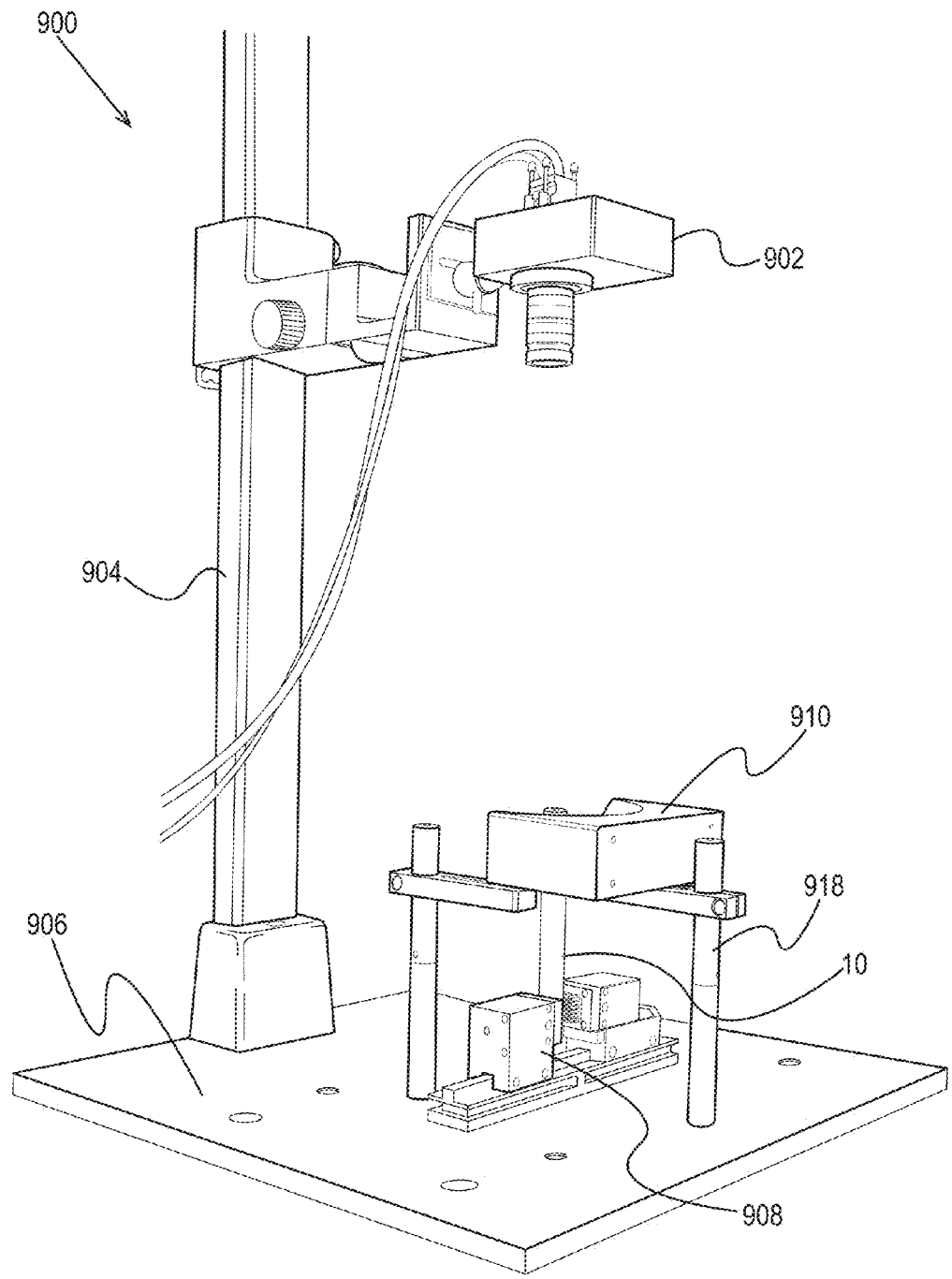
FIG. 12 is a perspective view of a Visible Projected Angle test apparatus according to one embodiment illustrated and described herein.

FIG. 12 illustrates a Visible Projected Angle test apparatus used to measure Total Visible Projected Angle ($\phi_T$). The Visible Projected Angle test apparatus 900 includes a luminance measuring color camera 902 with computer interface (a suitable camera is a LMK 98-4 Color luminance measuring color camera and LMK Labsoft software). The test apparatus 900 also includes a camera stand 904 (steel stand with a minimum height of 1100 mm) to firmly hold the camera and allow the camera 902 to be moved vertically; a base plate 906 (400×500 steel plate) and a toothbrush holder 908 (X-Grip XS available from Matrix GmbH Stuttgart) mounted to the base plate 906. The test apparatus 900 further includes a half cone 910 (an example of a suitable material for construction of the half cone is optical polytetrafluoroethylene (PTFE) available from Berghof Products, Germany) and at least two support stands 918 (aluminum stands with a height of 200 mm) to support half cone 910.

Figure 13A:
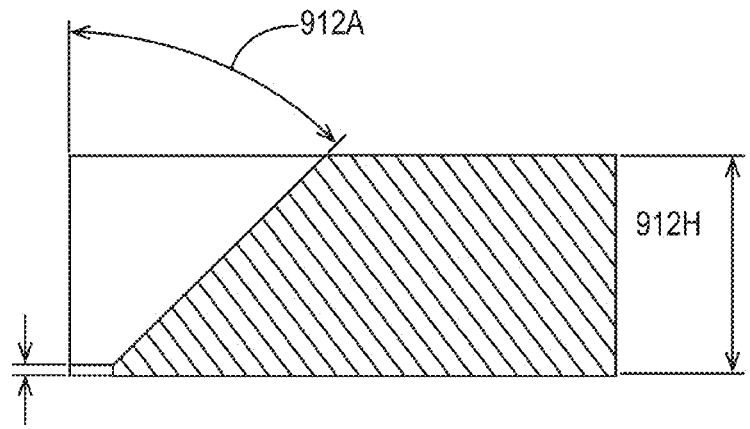
FIG. 13A is a cross-sectional view of a half cone according to one embodiment illustrated and described herein.
Figure 13B:
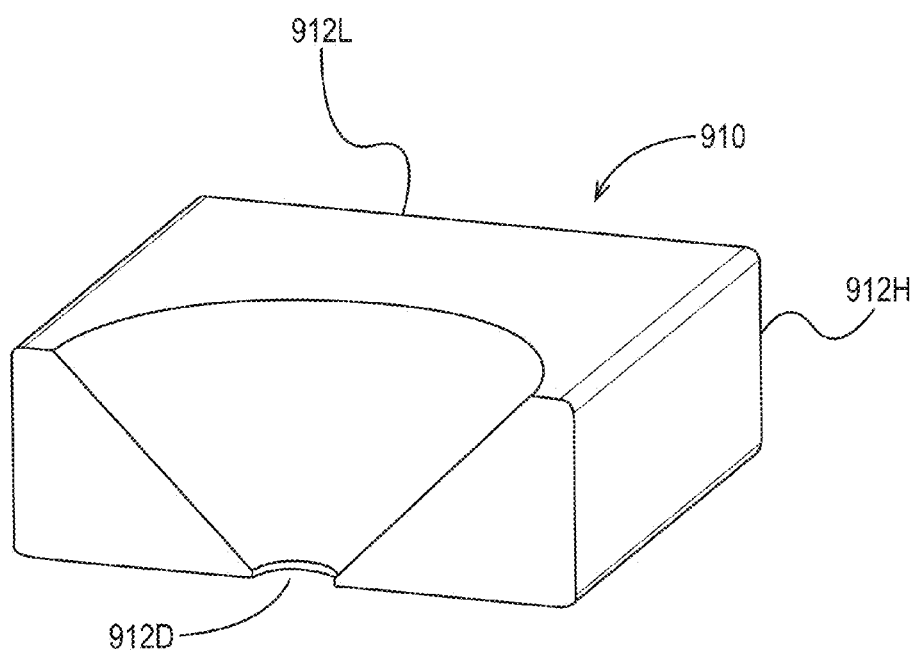
FIG. 13B is a perspective view of a half cone according to one embodiment illustrated and described herein.

FIGS. 13A and 13B illustrate half cone 910. The half cone 910 defines a bottom diameter 912D of 32 mm; a height 912H of 80 mm; a length 912L of 200 mm; and a half cone angle 912A of 45 degrees.

Figure 14A:
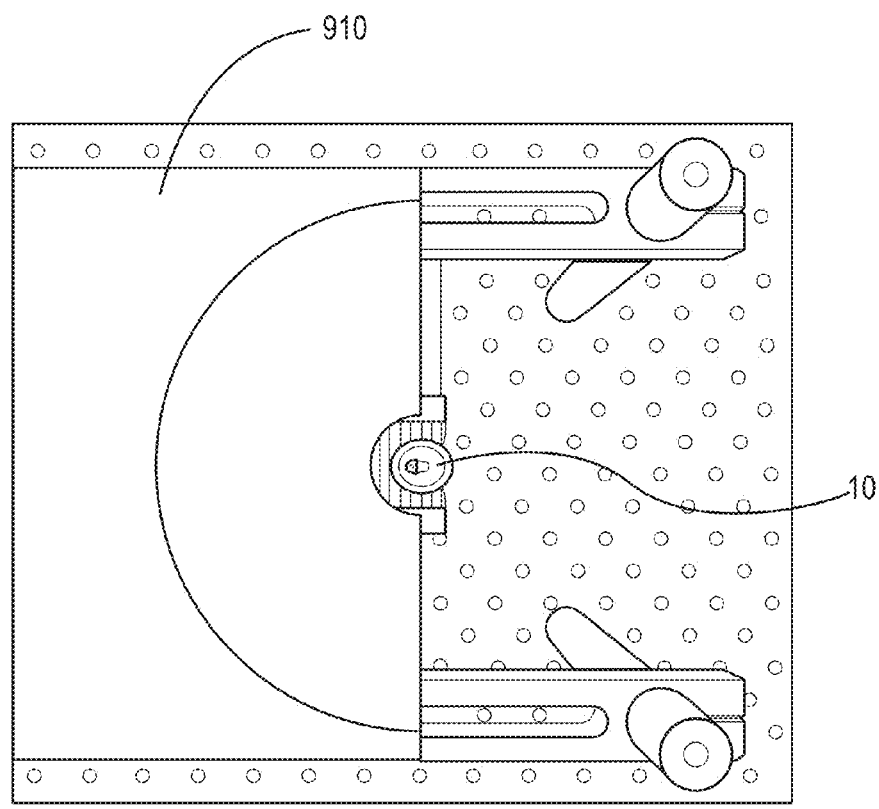
FIG. 14A is a top plan view of an oral hygiene implement centered in a half cone according to one embodiment illustrated and described herein.

Position the toothbrush with indication element so that it is centered in the half cone with the front-facing surface towards the half cone 910, as shown in FIG. 14A. Additionally, the toothbrush is held in the half cone by toothbrush holder 908 so that the bottom edge of the indication element is 10 mm above the lower edge of the half cone.

Figure 15:
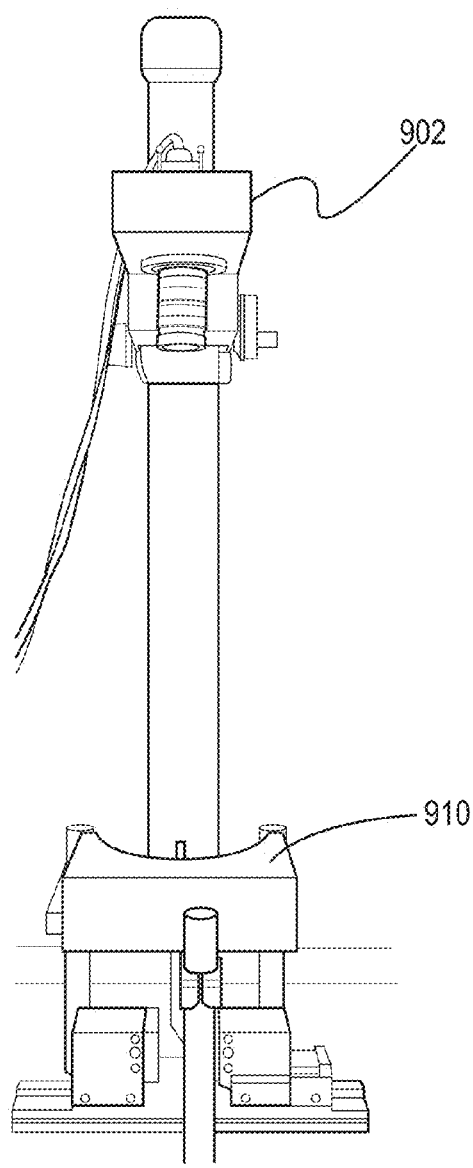
FIG. 15 is a front view of a camera centered above a half cone as part of a Visible Projected Angle test apparatus according to one embodiment illustrated and described herein.
Figure 16A:
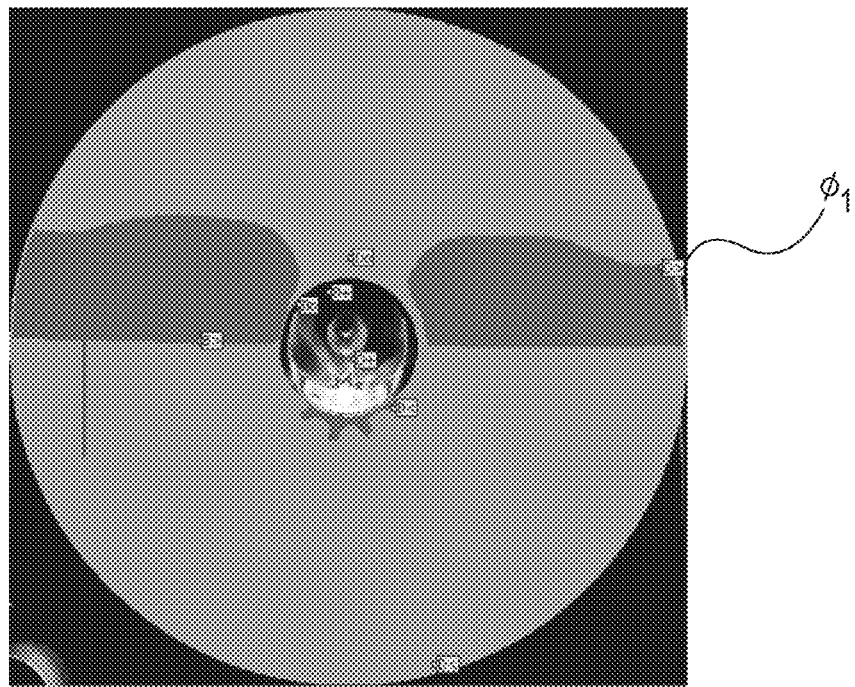
FIG. 16A depicts Visible Projected Angle $\phi_1$ for Example 1 of Table 1.
Figure 16B:
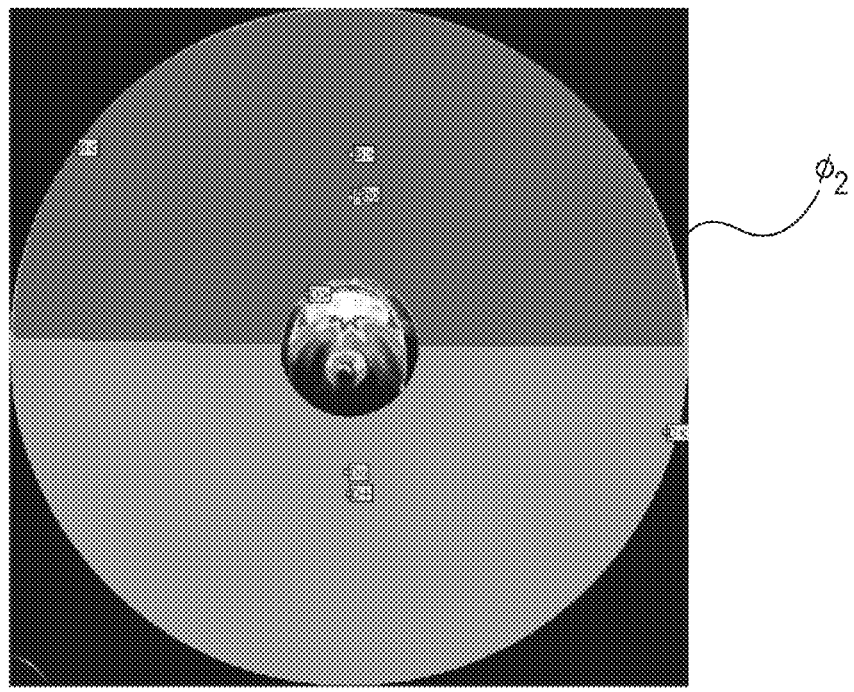
FIG. 16B depicts Visible Projected Angle $\phi_2$ for Example 1 of Table 1.
Figure 17A:
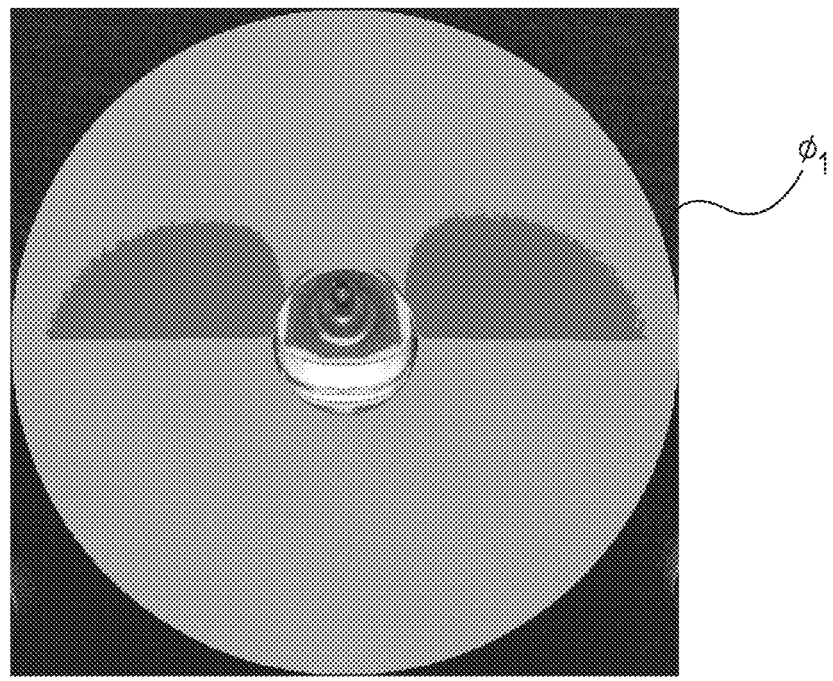
FIG. 17A depicts Visible Projected Angle $\phi_1$ for Example 2 of Table 1.
Figure 17B:
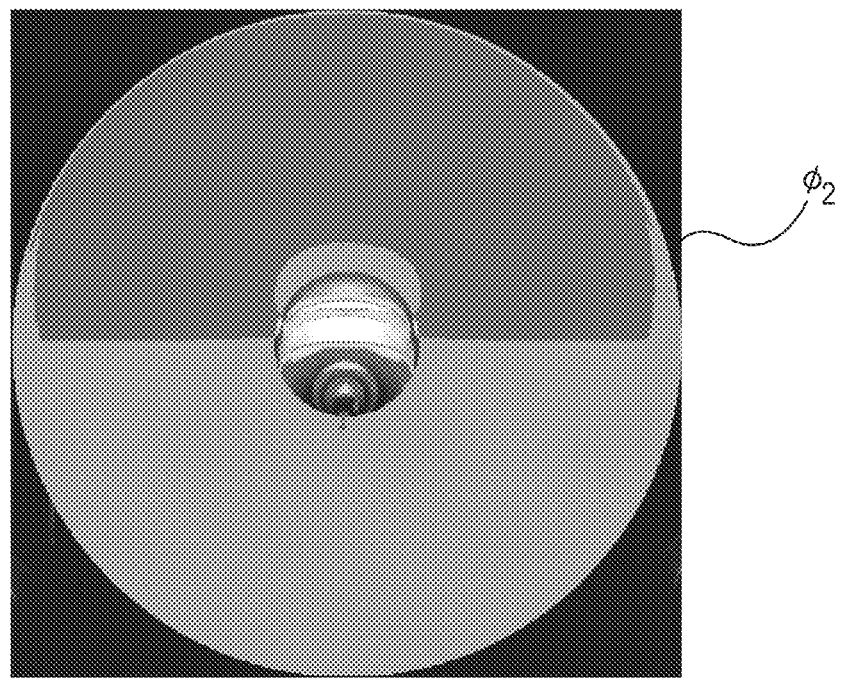
FIG. 17B depicts Visible Projected Angle $\phi_2$ for Example 2 of Table 1.
Figure 18:
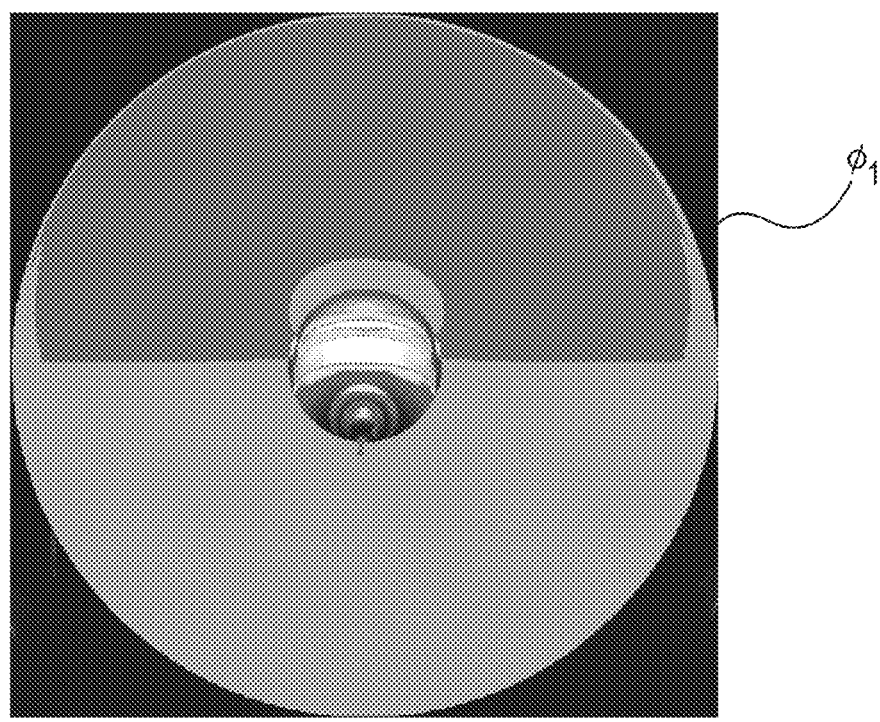
FIG. 18 depicts Visible Projected Angle $\phi_1$ for Example 3 of Table 1.
Figure 19A:
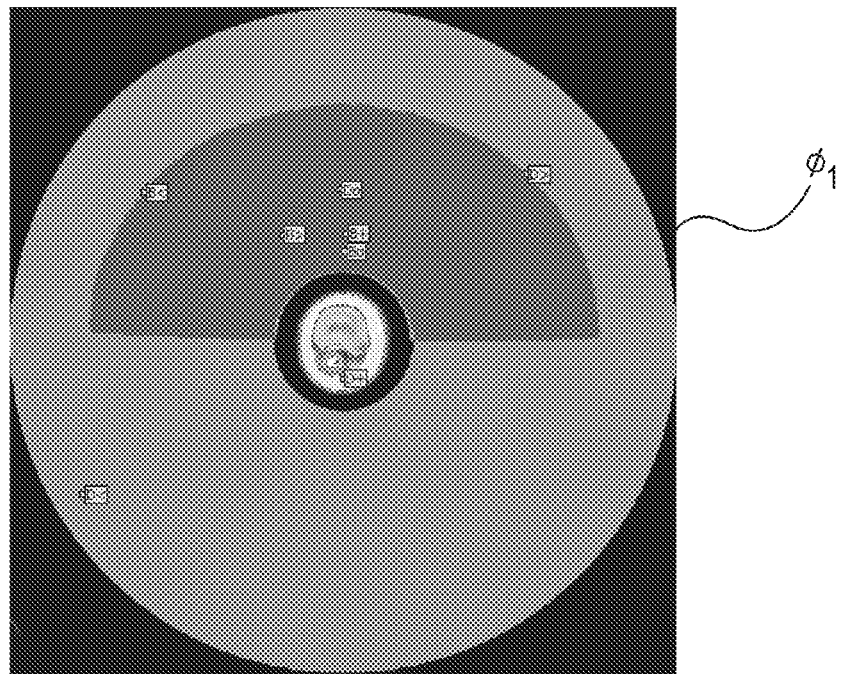
FIG. 19A depicts Visible Projected Angle $\phi_1$ for Example 4 of Table 1.
Figure 19B:
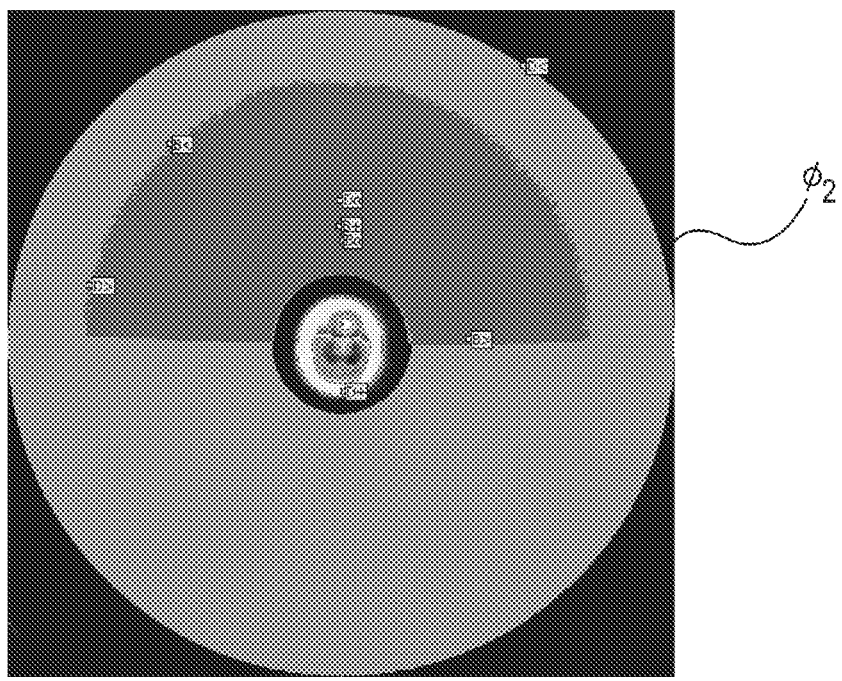
FIG. 19B depicts Visible Projected Angle $\phi_2$ for Example 4 of Table 1.

Position the camera 902 so that the lens is centered above the half cone 910 and in line with the center axis of the half cone 910, as shown in FIG. 15. The height of the camera 902 should be set to 780 mm measured from the lower edge of the lens to the top edge of the half cone 910.

Open the LMK Labsoft software and set the exposure time to "Automatic"" under "Main Menu: "Camera"→"Exposure Time"

Using the "Live Mode" in the LMK Labsoft software, turn on the indication element on the toothbrush and using the focus wheel on the camera 902, focus on the area where the light is reflected in the cone. An object, such as a pencil, may be placed near the reflection to be used as a reference to assist when adjusting the focus. When the image is in focus, record the selected scale factor from the camera lens and enter it into the LMK Labsoft software under "Main menu: Camera/Recalibration; A new window "Capture Properties" opens, choose tab "Recalibration" and insert scale factor under "Capture Settings; Focus."

With the LMK Labsoft software still open, select "Camera" from the menu screen and then "Live". With the image on the computer monitor, right click on the image and select "New Circular Ring" from the list. Adjust the circular ring so that the outer circle is aligned with the top edge of the cone and the inner circle is aligned with the bottom edge of the cone. Assure that the toothbrush is in the center of the cone/inner circle.

While the indication element remains on, switch off the ambient light. Using the "HighDyn" mode on the camera 902, take a picture of the toothbrush. Save the picture to computer. Rotate the toothbrush 180 degrees along its longitudinal axis so that the back-facing surface of the toothbrush is oriented towards the half cone and take another picture. Save the picture to computer.

Both pictures are then processed using the Labsoft software. In particular, choose the tab "Luminance image" and select the circular ring. Right click using the computer mouse and select "Statistics" and then "Luminance object." Next, click on "Properties Dialog" and under "Parameter" insert "1" next to "Threshold 0" and insert "1" next to "Threshold 1" and click "Accept." Repeat this for both pictures. This step sets the minimum threshold intensity of the projected visible light on the surface of the half cone at 1 cd/m².

Thus, an area with a luminance of equal to or greater than 1 cd/m² will appear darker (blue if in color picture) and an area with a luminance of less than 1 cd/m² will appear lighter (red if in color picture).

Print the pictures. Measure the area of picture 1 with a luminance equal to or greater than 1 cd/m² (i.e. the area that is a darker shade—blue if color picture) with a protractor (See FIGS. 16A to 19). This value is the Visible Projected Angle ($\phi_1$) for the first picture. Next, measure the area of picture 2 with a luminance equal to or greater than 1 cd/m² (i.e. the area that is a darker shade—blue if color picture) with a protractor. This value is the Visible Projected Angle ($\phi_2$) for the second picture. Once ($\phi_1$) and ($\phi_2$) are calculated for each picture, the Total Visible Projected Angle ($\phi_T$) can be obtained by the formula: Total Visible Projected Angle ($\phi_T$)=($\phi_1$+$\phi_2$).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral hygiene implement comprising:
   a) a handle;
   b) a head including a plurality of contact elements;
   c) a neck disposed between the handle and the head;
   d) an indication element; and
   e) an electromagnetic energy output source in electromagnetic communication with the indication element, wherein the electromagnetic energy is directed from the output source to the indication element such that a Total Visible Projected Angle ($\phi_T$) of the oral hygiene implement is greater than about 300 degrees;
   f) a transmission element in electromagnetic energy communication with the output source;
   g) a transmission element ring having a bottom edge and in electromagnetic energy communication with the transmission element; and
   h) a reflective core disposed within the transmission element, wherein the reflective core redirects electromagnetic energy from the output source to the indication element.

2. The oral hygiene implement according to claim 1, wherein the Total Visible Projected Angle ($\phi_T$) is greater than about 320 degrees.

3. The oral hygiene implement according to claim 1, wherein the Total Visible Projected Angle ($\phi_T$) is greater than about 340 degrees.

4. The oral hygiene implement according to claim 1, wherein Visible Projected Angle ($\phi_1$) is greater than about 130 degrees.

5. The oral hygiene implement according to claim 1, wherein the indication element is positioned between the handle and neck.

6. The oral hygiene implement according to claim 1, wherein the reflective core includes one or more reflective faces.

7. The oral hygiene implement according to claim 1, wherein the transmission element ring includes one or more surface contours.

8. The oral hygiene implement according to claim 7, wherein the transmission element ring includes at least three surface contours and the distance between the surface contours varies.

9. The oral hygiene implement according to claim 7, wherein the one or more surface contours is positioned on the bottom edge of the transmission element ring.

10. The oral hygiene implement according to claim 1, wherein the implement is a manual toothbrush.

11. The oral hygiene implement according to claim 1, wherein the implement is a powered toothbrush.

12. The oral hygiene implement according to claim 1, wherein the indication element has a luminance of at least about 1 cd/m$^2$.

13. The oral hygiene implement according to claim 1, wherein the indication element has a luminance of at least about 2 cd/m$^2$.

14. An oral hygiene implement comprising:
 a) a handle;
 b) a head including a plurality of contact elements;
 c) a neck disposed between the handle and the head;
 d) an indication element; and
 e) an electromagnetic energy output source in electromagnetic communication with the indication element, wherein the electromagnetic energy is directed from the output source to the indication element such that a Visible Projected Angle ($\phi_1$) of the oral hygiene implement is greater than about 150 degrees;
 f) a transmission element in electromagnetic energy communication with the output source;
 g) a transmission element ring having a bottom edge and in electromagnetic energy communication with the transmission element; and
 h) a reflective core disposed within the transmission element, wherein the reflective core redirects electromagnetic energy from the output source to the indication element.

15. The oral hygiene implement according to claim 14, wherein the indication element is positioned between the handle and neck.

16. The oral hygiene implement according to claim 14, wherein the indication element has a luminance of from about 1 cd/m$^2$ to about 5 cd/m$^2$.

* * * * *